US008468891B2

(12) United States Patent
Chekan et al.

(10) Patent No.: US 8,468,891 B2
(45) Date of Patent: Jun. 25, 2013

(54) TISSUE PROCESSING DEVICE WITH ULTRASONIC MEASURING CHAMBER

(75) Inventors: Edward G. Chekan, Cincinnati, OH (US); Kevin L. Houser, Springboro, OH (US); Robert E. Sackett, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 516 days.

(21) Appl. No.: 12/778,769

(22) Filed: May 12, 2010

(65) Prior Publication Data

US 2011/0281297 A1 Nov. 17, 2011

(51) Int. Cl.
*G01N 29/00* (2006.01)
(52) U.S. Cl.
USPC .............................. 73/649; 73/61.75
(58) Field of Classification Search
USPC ................. 73/649, 61.75, 28.01, 597, 602
See application file for complete search history.

(56) References Cited

U.S. PATENT DOCUMENTS

| | | | |
|---|---|---|---|
| 5,526,822 A | 6/1996 | Burbank et al. | |
| 5,694,951 A | 12/1997 | Bonutti | |
| 5,823,962 A | 10/1998 | Schaetzle | |
| 5,831,150 A | 11/1998 | Sowerby et al. | |
| 6,086,544 A | 7/2000 | Hibner et al. | |
| 6,489,706 B2 | 12/2002 | Sliwa, Jr. et al. | |
| 6,508,855 B2 | 1/2003 | Gardner et al. | |
| 6,627,421 B1 | 9/2003 | Unger et al. | |
| 6,990,982 B1 | 1/2006 | Bonutti | |
| 7,115,100 B2 | 10/2006 | McRury et al. | |
| 7,442,171 B2 | 10/2008 | Stephens et al. | |
| 7,611,473 B2 | 11/2009 | Boock et al. | |
| 2004/0065599 A1 | 4/2004 | Lal et al. | |
| 2004/0078090 A1 | 4/2004 | Binette et al. | |
| 2004/0193071 A1 | 9/2004 | Binette et al. | |
| 2005/0038520 A1 | 2/2005 | Binette et al. | |
| 2005/0113736 A1 | 5/2005 | Orr et al. | |
| 2005/0125077 A1 | 6/2005 | Harmon et al. | |
| 2005/0139704 A1 | 6/2005 | Liao et al. | |
| 2005/0262927 A1 | 12/2005 | Scott | |

(Continued)

FOREIGN PATENT DOCUMENTS

| | | |
|---|---|---|
| EP | 0 418 979 | 3/1991 |
| WO | WO 98/09574 | 3/1998 |
| WO | WO 2007/083295 | 7/2007 |

OTHER PUBLICATIONS

International Search Report and Written Opinion dated Aug. 11, 2011 for Application No. PCT/US11/036261.
International Search Report and Written Opinion dated Sep. 1, 2011 for Application No. PCT/US2011/036277.
U.S. Appl. No. 12/483,305, filed Jun. 12, 2009, Hibner et al.
Cents, A.H.G., et al., "Measuring Bubble, Drop and Particle Sizes in Multiphase Systems with Ultrasound," AIChE Journal, vol. 50(11) (Nov. 2004) pp. 2750-2762.
McDonnell, M., "Moving Particles with Ultrasonic Standing Waves," DSTL Codex Journal, Issue 1 (Summer 2008) pp. 1-4.
Restriction Requirement dated Sep. 25, 2012 for U.S. Appl. No. 12/778,806.

*Primary Examiner* — J M Saint Surin
(74) *Attorney, Agent, or Firm* — Frost Brown Todd LLC

(57) ABSTRACT

A device is operable to measure the size of tissue particles. The device includes a reservoir for receiving tissue particles and an ultrasonic transducer. The ultrasonic transducer is operable to emit ultrasonic energy toward tissue particles in the reservoir. Control circuitry is operable to process ultrasonic energy received from the ultrasonic transducer to determine the size of tissue particles in the reservoir. If the tissue particles are larger than a predetermined size range, the particles may be minced to reduce their size. If the tissue particles are smaller than a predetermined size range, the particles may be disposed of. It the tissue particles have a size within a predetermined range, they may be processed further, such as by stimulating the tissue particles and dewatering the tissue particles. The tissue particles may then be incorporated in a medical fluid and be therapeutically administered to a patient.

19 Claims, 9 Drawing Sheets

U.S. PATENT DOCUMENTS

| | | |
|---|---|---|
| 2008/0071385 A1 | 3/2008 | Binette et al. |
| 2008/0214955 A1 | 9/2008 | Speeg et al. |
| 2008/0234715 A1 | 9/2008 | Pesce et al. |
| 2008/0294054 A1 | 11/2008 | Asagiri et al. |
| 2008/0311219 A1 | 12/2008 | Gosiewska et al. |
| 2009/0034370 A1 | 2/2009 | Guo |
| 2009/0051350 A1 | 2/2009 | Becker et al. |
| 2010/0015682 A1 | 1/2010 | Sasaki et al. |
| 2010/0160819 A1 | 6/2010 | Parihar et al. |

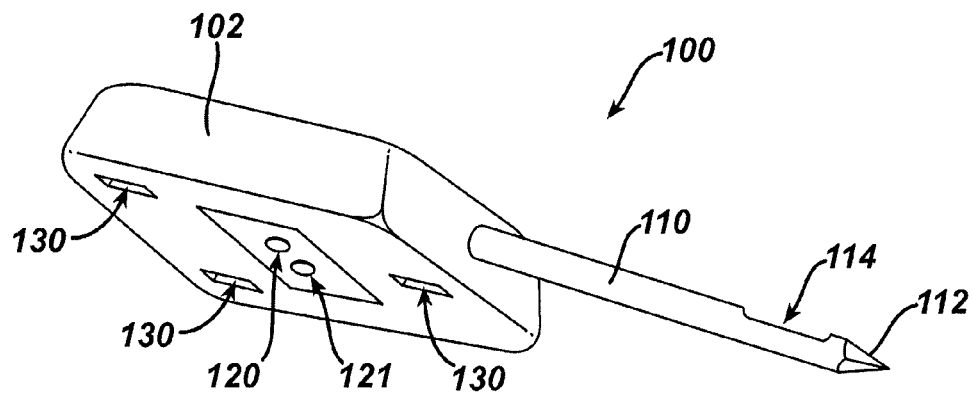
FIG. 3
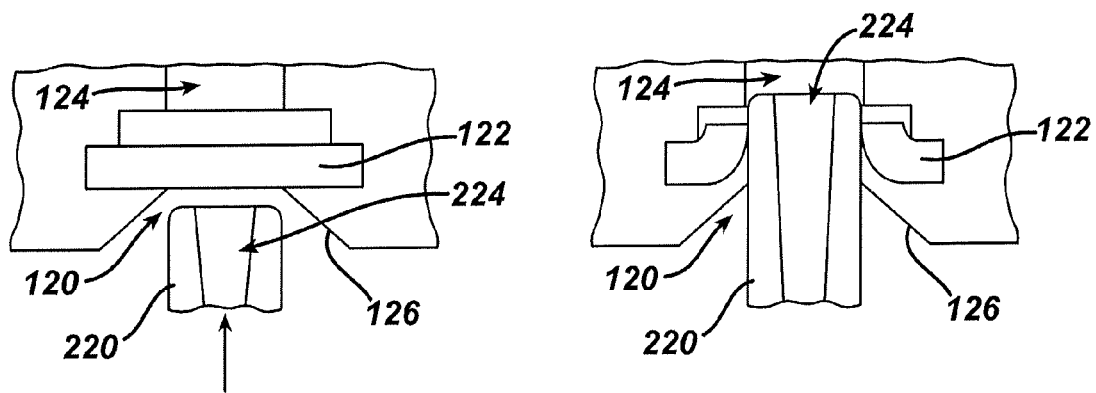
FIG. 4A     FIG. 4B

TISSUE PROCESSING DEVICE WITH ULTRASONIC MEASURING CHAMBER

BACKGROUND

Fistulae can occur for a variety of reasons, such as, from a congenital defect, as a result of inflammatory bowel disease such as Crohn's disease, some sort of trauma, or as a side effect from a surgical procedure. Additionally, several different types of fistulae can occur in humans, for example, urethro-vaginal fistulae, vesico-vaginal fistulae, tracheo-esophageal fistulae, gastrointestinal fistulae, for example gastrocutaneous, enterocutaneous and colocutaneous fistulae, and any number of anorectal fistulae such as recto-vaginal fistula, recto-vesical fistulae, recto-urethral fistulae, and recto-prostatic fistulae. When fistulas form, they can track between intestinal segments or between an intestinal segment and other organs (e.g., bladder, vagina, etc.), adjacent tissue, or the skin. Fistulas are classified as internal when they communicate with adjacent organs (e.g., entero-enteric and rectovaginal fistulas, etc.) and external when they communicate with the dermal surface (e.g., enterocutaneous, peristomal and perianal fistulas, etc.).

Promoting and improving tissue healing around the fistula opening and in the fistula tract may be an important aspect of fistulae medical treatments. For instance, promoting and improving tissue healing may lead to quicker recovery times and lessen the opportunity for infection, particularly in a post-surgical context. Some advancements in the medical arts pertaining to systems, methods, and devices to promote and improve tissue healing in patients aim to add active biological components (e.g., tissue particles, stem cells, other types of cells, etc.) to a wound site (e.g., surgical site, accidental trauma site, etc.) or other defect site (e.g., caused by disease or other condition, etc.) to promote tissue regeneration or accelerate tissue healing. When adding biological components to a site, such components may be added independently or as part of a specifically designed matrix or other mixture depending on the condition being treated and goals of the treatment. Some examples of cell-based therapy technology are disclosed in U.S. Pub. No. 2008/0311219, entitled "Tissue Fragment Compositions for the Treatment of Incontinence," published Dec. 18, 2008, the disclosure of which is incorporated by reference herein. Additional examples of cell-based therapy technology are disclosed in U.S. Pub. No. 2004/0078090, entitled "Biocompatible Scaffolds with Tissue Fragments," published Apr. 22, 2004, the disclosure of which is incorporated by reference herein. Additional examples of cell-based therapy technology are disclosed in U.S. Pub. No. 2008/0071385, entitled "Conformable Tissue Repair Implant Capable of Injection Delivery," published Mar. 20, 2008, the disclosure of which is incorporated by reference herein.

Regardless of how the active biological components are delivered or applied to a site, the biological components must first be obtained and prepared. One approach for obtaining such biological components is to harvest the desired components from a healthy tissue specimen (e.g., in an adult human). Examples of devices and associated methods for collecting and processing harvested tissue are disclosed in U.S. Pub. No. 2004/0193071, entitled "Tissue Collection Device and Methods," published Sep. 30, 2004, the disclosure of which is incorporated by reference herein. Additional examples of devices and associated methods for collecting and processing harvested tissue are disclosed in U.S. Pub. No. 2005/0038520, entitled "Method and Apparatus for Resurfacing an Articular Surface," published Feb. 17, 2005, the disclosure of which is incorporated by reference herein. Additional examples of devices and associated methods for collecting and processing harvested tissue are disclosed in U.S. Pat. No. 7,611,473, entitled "Tissue Extraction and Maceration Device," issued Nov. 3, 2009, the disclosure of which is incorporated by reference herein. Additional examples of devices and associated methods for collecting and processing harvested tissue are disclosed in U.S. Pub. No. 2008/0234715, entitled "Tissue Extraction and Collection Device," published Sep. 25, 2008, the disclosure of which is incorporated by reference herein. Additional examples of devices and associated methods for processing harvested tissue are disclosed in U.S. Pub. No. 2005/0125077, entitled "Viable Tissue Repair Implants and Methods of Use," published Jun. 9, 2005, the disclosure of which is incorporated by reference herein. Additional examples of devices and associated methods for collecting and processing harvested tissue are disclosed in U.S. Pat. No. 5,694,951, entitled "Method for Tissue Removal and Transplantation," issued Dec. 9, 1997, the disclosure of which is incorporated by reference herein. Additional examples of devices and associated methods for collecting and processing harvested tissue are disclosed in U.S. Pat. No. 6,990,982, entitled "Method for Harvesting and Processing Cells from Tissue Fragments," issued Jan. 31, 2006, the disclosure of which is incorporated by reference herein. Additional examples of devices and associated methods for collecting and processing harvested tissue are disclosed in U.S. Pat. No. 7,115,100, entitled "Tissue Biopsy and Processing Device," issued Oct. 3, 2006, the disclosure of which is incorporated by reference herein.

Once harvested and suitably processed (e.g., incorporated with a scaffold, etc.), biological material such as tissue fragments may be applied to a wound site or other type of site within the human body in a variety of ways. Various methods and devices for applying such biological material are disclosed in one or more of the U.S. patent references cited above. Additional methods and devices for applying such biological material are disclosed in U.S. Pub. No. 2005/0113736, entitled "Arthroscopic Tissue Scaffold Delivery Device," published May 26, 2005, the disclosure of which is incorporated by reference herein.

While a variety of devices and techniques may exist for harvesting, processing, and applying biological components from a tissue specimen, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

FIG. 3 depicts a perspective view of an exemplary tissue harvesting device of the tissue processing system of FIG. 1.

FIG. 4A depicts a partial view of a port of the tissue harvesting device of FIG. 3 separated from a port of a console of the tissue processing system of FIG. 1.

FIG. 4B depicts a partial view of the ports of FIG. 4A coupled together.

Figure 1:
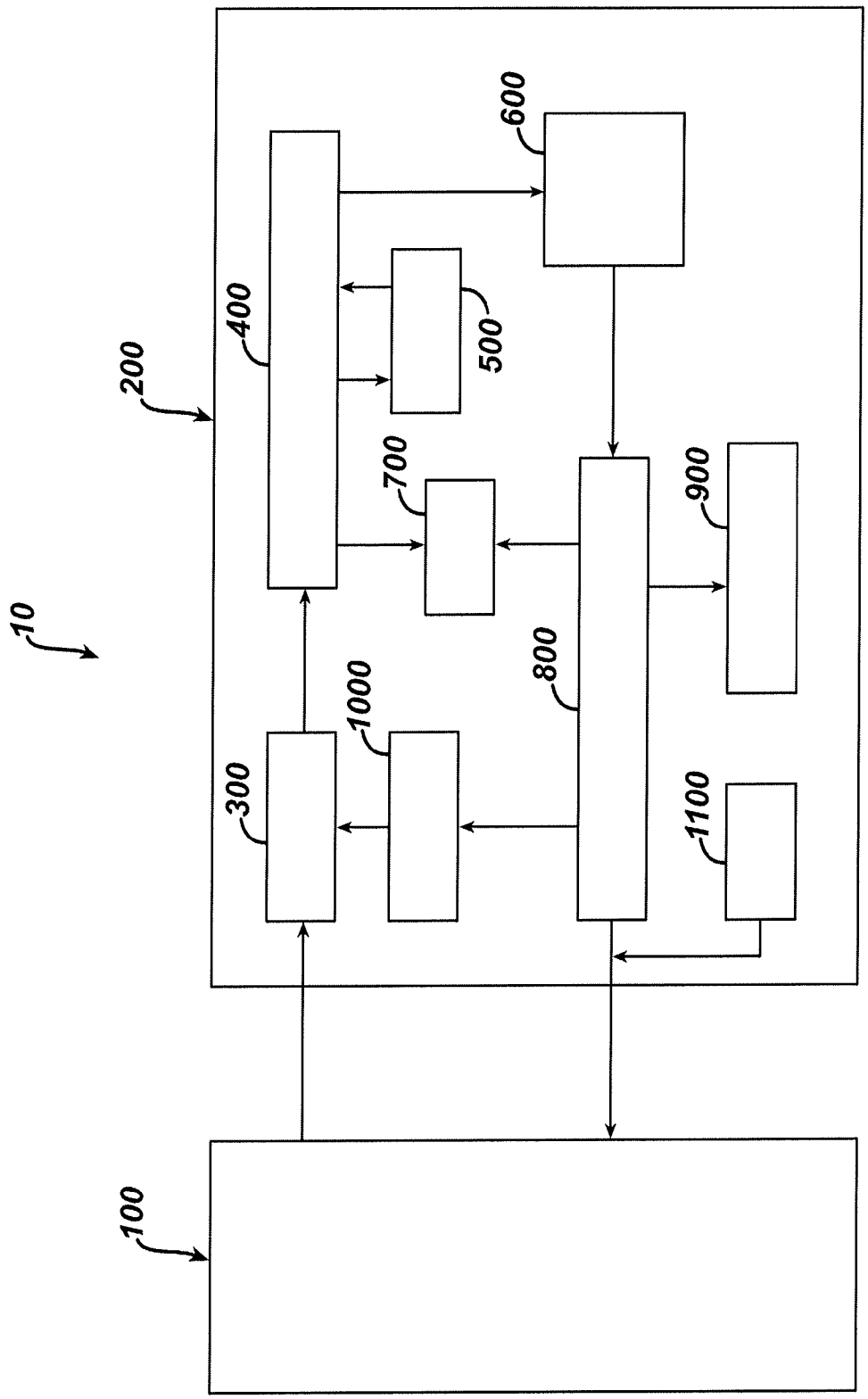
FIG. 1 depicts a diagrammatic view of an exemplary tissue processing system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Overview of Exemplary Treatment Compositions, Devices, and Methods

Examples described herein include devices that are operable to harvest tissue, mince or morcellate tissue, mix tissue particles with other medical fluid components, and/or dispense a medical fluid at a target site in a patient. As described in greater detail below, the medical fluid may include any of a variety of biocompatible materials that accelerate tissue healing, promote tissue regeneration, and/or provide other results. As used herein, the terms "tissue treatment composition," "tissue repair composition," and "medical fluid" should be read interchangeably. It should also be understood that a tissue treatment composition or medical fluid as referred to herein may have any suitable consistency, including but not limited to the consistency of a slurry.

A medical fluid as referred to herein may be derived from any biocompatible material, including but not limited to synthetic or natural polymers. The consistency of the medical fluid may be viscous, or gel-like, that of a slurry composed of microparticles, or any other suitable consistency. By way of example only, any fluid consistency that may permit injection through a catheter may be used. The medical fluid may also provide adhesive characteristics, such that once it is injected at a target site (e.g., into a fistula), the fluid coagulates or gels (e.g., allowing for a plug to be retained within a fistula). The medical fluid of the present example is also able to support cell migration and proliferation such that healing at a target site in a patient can occur. The fluid is suitable to be mixed with biological materials. Examples of medical fluid components include but are not limited to thrombin, platelet poor plasma (PPP) platelet rich plasma (PRP), starch, chitosan, alginate, fibrin, polysaccharide, cellulose, collagen, gelatin-resorcin-formalin adhesive, oxidized cellulose, mussel-based adhesive, poly (amino acid), agarose, amylose, hyaluronan, polyhydroxybutyrate (PHB), hyaluronic acid, poly(vinyl pyrrolidone) (PVP), poly(vinyl alcohol) (PVA), polylactide (PLA), polyglycolide (PGA), polycaprolactone (PCL), and their copolymers, VICRYL® (Ethicon, Inc., Somerville, N.J.), MONOCRYL material, PANACRYL (Ethicon, Inc., Somerville, N.J.), and/or any other material suitable to be mixed with biological material and introduced to a wound or defect site, including combinations of materials. Other suitable compounds, materials, substances, etc., that may be used in a medical fluid will be apparent to those of ordinary skill in the art in view of the teachings herein.

By way of example only, one or more components in a medical fluid or tissue treatment composition may comprise at least one viable tissue fragment having one or more viable cells that, once applied, can proliferate and integrate with tissue at a target site in a patient. For instance, viable cells may migrate out of a tissue particle and populate a scaffold material, which may be positioned at a target site in a patient. Such tissue fragments may have been harvested from the same patient in whom they are reapplied; or may have been harvested from another person or source. The tissue fragments may comprise autogenic tissue, allogenic tissue, xenogenic tissue, mixtures of any of the foregoing, and/or any other type(s) of tissue. The tissue fragments may include, for example, one or more of the following tissues or tissue components: stem cells, cartilage tissue, meniscal tissue, ligament tissue, tendon tissue, skin tissue, muscle tissue (e.g., from the patient's thigh, etc.), periosteal tissue, pericardial tissue, synovial tissue, fat tissue, bone marrow, bladder tissue, umbilical tissue, embryonic tissue, vascular tissue, blood and combinations thereof. Of course, any other suitable type of tissue may be used, including any suitable combination of tissue types. In some versions, the type of tissue used is selected from a tissue type most resembling the tissue at, near, or surrounding the target site (e.g., fistula, etc.).

Tissue for providing at least one viable tissue fragment may be obtained using any of a variety of tissue biopsy devices or using other types of tissue harvesting devices or techniques. Exemplary biopsy devices include those taught in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2007/0118048, issued as U.S. Pat. No. 7,442,171, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Non-Provisional patent application Ser. No. 12/337,942, entitled "Biopsy Device with Central Thumbwheel," filed Dec. 18, 2008, published as U.S. Pub. No. 2010/0160819; and U.S. Non-Provisional patent application Ser. No. 12/483,305, entitled "Tetherless Biopsy Device with Reusable Portion," filed Jun. 12, 2009, issued as U.S. Pat. No. 8,206,316. The disclosure of each of the above-cited U.S. Patents, U.S. Patent Application Publications, and U.S. Non-Provisional Patent Applications is incorporated by reference herein. Such biopsy devices may be used to extract a plurality of tissue specimens from one or more sites in a single patient. It should also be understood that any suitable device described in any other reference that is cited herein may be used to harvest tissue. Additional examples of devices that may be used to harvest tissue will be described in greater detail below. Other examples will be apparent to those of ordinary skill in the art in view of the teachings herein. Tissue harvesting sites may include the same sites in which tissue is reapplied as part of a treatment. In addition or in the alternative, tissue may be harvested from one site and then reapplied at some other site as part of a treatment. In some versions, the tissue is reapplied in the same patient from whom the tissue was originally harvested. In some other versions, the tissue is applied in a patient who is different from the patient from whom the tissue was originally harvested.

A tissue specimen may be obtained under aseptic conditions, and then processed under sterile conditions to create a suspension having at least one minced, or finely divided, tissue fragment. In other words, harvested tissue may be diced, minced or morcellated, and/or otherwise processed. Harvested tissue specimens may be minced and otherwise processed in any of a variety of ways. For instance, examples of tissue mincing and processing are described in U.S. Pub. No. 2004/0078090, the disclosure of which is incorporated by reference herein. Alternatively, merely exemplary non-conventional devices and techniques that may be used to mince and process tissue will be described in greater detail below, while other examples will be apparent to those of ordinary skill in the art in view of the teachings herein. In order to ensure viability of the tissue, agitators or other features of a mincing and/or mixing device may be designed to sever and mix (rather than crush or compress) the tissue. In some settings, tissue specimens may be minced and/or mixed in a standard cell culture medium, either in the presence or absence of serum. Tissue fragments may also be contacted with a matrix-digesting enzyme to facilitate cell migration out of an extracellular matrix surrounding the cells. Suitable matrix-digesting enzymes that may be used in some settings include, but are not limited to, collagenase, chondroitinase, trypsin, elastase, hyaluronidase, peptidase, thermolysin, and protease. The size of each tissue fragment may vary depending on the target location, method for delivering the treatment composition to the target site, and/or based on various other considerations. For example, the tissue fragment size may be chosen to enhance the ability of regenerative cells (e.g., fibroblasts) in the tissue fragments to migrate out of the tissue fragments, and/or to limit or prevent the destruction of cell integrity. In some settings, ideal tissue fragments are between approximately 200 microns and approximately 500 microns in size. As another merely illustrative example, ideal tissue fragments may be sized within the range of approximately 0.05 mm$^3$ and approximately 2 mm$^3$; or more particularly between approximately 0.05 mm$^3$ and approximately 1 mm$^3$. Of course, various other tissue fragment sizes may be ideal in various different settings.

In some versions, a medical fluid may comprise minced tissue fragments suspended in a biocompatible carrier. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include the following: proteins such as collagen, collagen gel, elastin, thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, Matrigel or atelocollagen; polysaccharides such as pectin, cellulose, oxidized regenerated cellulose, chitin, chitosan, agarose, or hyaluronic acid; polynucleotides such as ribonucleic acids or deoxyribonucleic acids; other materials such as alginate, cross-linked alginate, poly(N-isopropylacrylamide), poly(oxyalkylene), copolymers of poly(ethylene oxide)-poly(propylene oxide), poly(vinyl alcohol), polyacrylate, or monostearoyl glycerol co-Succinate/polyethylene glycol (MGSA/PEG) copolymers; and combinations of any of the foregoing. In addition to providing a flowable carrier solution for tissue fragments, a gelling agent(s) may also act as an adhesive that anchors the tissue repair composition at the target site. In some versions, an additional adhesive anchoring agent may be included in the tissue repair composition or medical fluid. Also, one or more cross-linking agents may be used in conjunction with one or more gelling agents in order to cross-link the gelling agent.

The concentration of tissue fragments in a carrier and/or one or more medical fluid components may vary depending on the target site location, method for delivering the treatment composition to the target site, and/or for various other reasons. By way of example, the ratio of tissue fragments to carrier (by volume) may be in the range of about 2:1 to about 6:1, or in the range of about 2:1 to about 3:1. The medical fluid may also include one more additional healing agents, such as biological components that accelerate healing and/or tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Similarly, in some versions where a scaffold plug is used in conjunction with a tissue repair composition, one or more of these additional biological components or additional treatment components may be provided on and/or within the scaffold plug. Some examples described herein may also include one or more adhesive agents in conjunction with viable tissue fragments.

As noted above, the harvested tissue may be combined with a scaffold material and/or other substances as part of a medical fluid, as described herein, for administration to the patient. To the extent that tissue is incorporated with a scaffold material, it should be understood that any suitable material or combination of materials may be used to provide a scaffold. By way of example only, scaffold material may include a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, hyaluronic acid, fibrin glue, fibrin clot, collagen gel, gelatin-resorcin-formalin adhesive, platelet rich plasma (PRP) gel, platelet poor plasma (PPP) gel, Matrigel, Monostearoyl Glycerol co-Succinate (MGSA), Monostearoyl Glycerol co-Succinate/polyethylene glycol (MGSA/PEG) copolymers, laminin, elastin, proteoglycans, polyhydroxybutyrate (PHB), poly(vinyl pyrrolidone) (PVP), polylactide (PLA), polyglycolide (PGA), polycaprolactone (PCL), and their copolymers, non-woven VICRYL® (Ethicon, Inc., Somerville, N.J.), MONOCRYL material, fibrin, non-woven poly-L-lactide, and non-woven PANACRYL (Ethicon, Inc., Somerville, N.J.). Polymers may include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly (ether urethane), and blends and copolymers thereof. Suitable synthetic polymers for use in examples described herein may also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides, and combinations thereof. Other suitable materials or combinations of materials that may be used will be apparent to those of ordinary skill in the art in view of the teachings herein. It should also be understood that tissue mixed with a scaffold material may have any suitable particle size, and that the resulting mixture may at least initially have the consistency of a slurry or have any other suitable consistency. In some versions, the tissue particles include an effective amount of viable cells that can migrate out of the tissue particle and populate the scaffold. The term "viable," as used herein, should be understood to include a tissue sample having one or more viable cells.

In some versions, one or more components in a medical fluid or tissue treatment composition comprise one or more healing agents that promote tissue regeneration at a target site (e.g., within a fistula) and/or accelerate tissue healing at the target site. Healing agents may include any of a variety of biocompatible materials that accelerate tissue healing and/or promote tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Some examples described herein may also include one or more adhesive agents in conjunction with viable tissue fragments.

Examples described herein relate to the repair (e.g., closing) of lumens in a patient, such as anal fistulas and other types of fistulas. In particular, examples described herein include devices used in at least part of a process to create and/or deliver tissue repair compositions or medical fluid into a lumen such as an anal fistula. It should be understood that anal fistulas and/or other types of fistulas may be relatively difficult to repair (e.g., close) in some settings. The goal of a surgical repair of an anal fistula may be to close the fistula with as little impact as possible on the sphincter muscles. In some settings, a tissue repair composition or medical fluid as described herein may be delivered into the fistula as a liquid composition, a flowable gel or paste, a scaffold plug, or a combination of the two or more of the foregoing (e.g., a porous scaffold plug loaded with a medical fluid composition, etc). Anal fistulas may also be repaired by injecting bioresorbable fibrin glue into the fistula that seals the fistula and promotes tissue growth across the fistula in order to provide permanent closure. Various bioresorbable plugs may also be used to repair anal fistulas. The plug may comprise, for example, collagen protein, tissue, stem cells, and/or other medical fluid components referred to herein; and the plug may be inserted into the fistula where it promotes tissue growth across the fistula as the plug dissolves. If desired, the plug may be secured in place using one or more fasteners and/or one or more adhesive agents. As another merely illustrative example, a medical fluid may be introduced within the fistula, and the medical fluid may eventually harden and then dissolve and/or be absorbed.

Prior to applying a medical fluid to a fistula, it may be desirable in some settings to debride the wall of a fistula (e.g., to remove epithelial cells, etc.), otherwise agitate the wall of the fistula, and/or otherwise treat the walls of the fistula. While examples herein are discussed in the context of an anorectal fistula, it should be understood that the following exemplary devices and techniques may be readily applied to various other types of fistulae. Similarly, while the present example relates to treatment of a fistula in a patient, it should also be understood that the following exemplary devices and techniques may be readily applied with respect to various other types of conditions in a patient. Other suitable ways in which the devices and techniques described herein may be used will be apparent to those of ordinary skill in the art in view of the teachings herein.

In some settings, a single device may be used to mince and mix tissue from a patient to form a medical fluid or later be incorporated in a medical fluid. Another device may be used to administer the medical fluid to the patient. In some instances, the device that is used to administer the medical fluid may be the same device that was used to initially harvest the tissue from the patient. Various examples of devices that may perform at least some of these functions will be described in greater detail below, while other examples will be apparent to those of ordinary skill in the art in view of the teachings herein.

As used herein, the term "fluid communication" (or in some contexts "communication") means that there is a path or route through which fluid (gas, liquid or other flowable material) may flow between two components, either directly or through one or more intermediate components. Similarly, the term "conduit" encompasses a conduit within or integrated with a valve. In other words, fluid communication between two components means that fluid can flow from one component to another but does not exclude an intermediate component (e.g., a valve, etc.) between the two recited components that are in fluid communication. Similarly, two or more components may be in mechanical "communication" with each other even if intermediate components are interposed between those two or more components.

II. Overview of Exemplary Tissue Processing System

Figure 2:
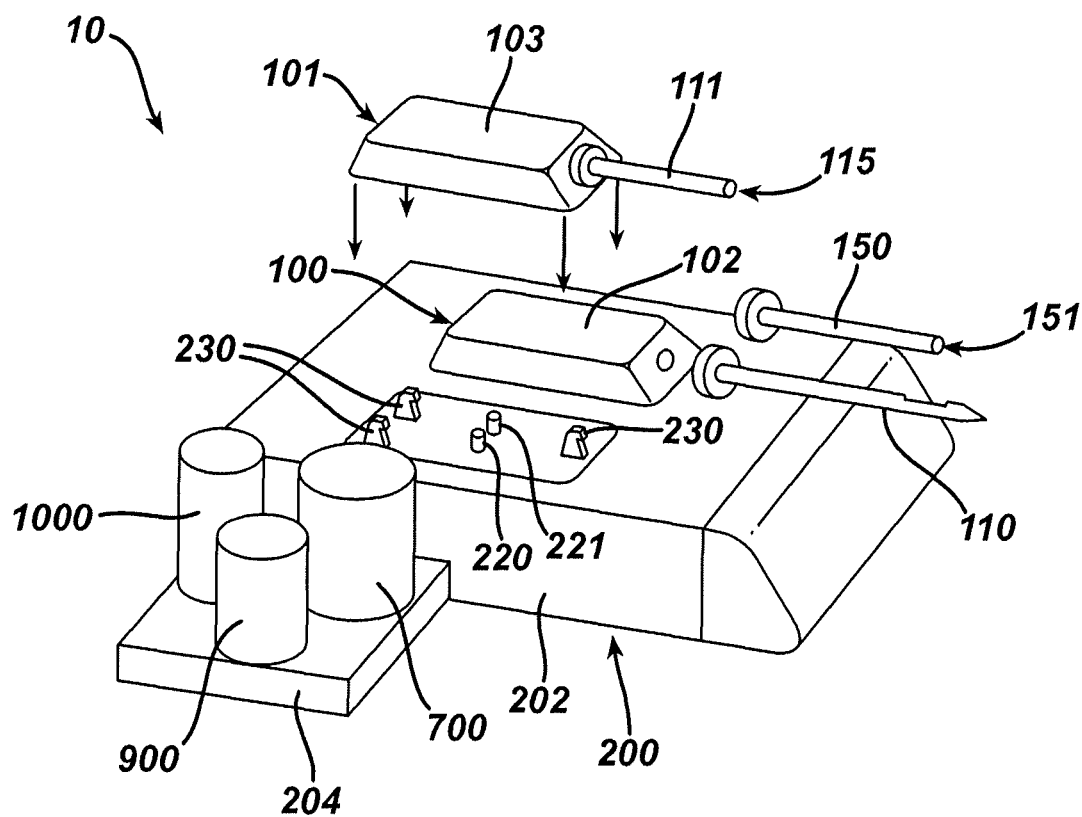
FIG. 2 depicts a perspective view of optional components of the tissue processing system of FIG. 1.

FIG. 1 shows various components of an exemplary tissue processing system (10). Each component of tissue processing system (10) will be described in greater detail below. It should be understood, however, that the components of tissue processing system (10) described below are mere examples. Each component may be varied in numerous ways as will be apparent to those of ordinary skill in the art in view of the teachings herein. Similarly, each component may be substituted, supplemented, or even omitted as desired. It should also be understood that the arrangement of components shown in FIG. 1 is merely illustrative; and that such components (and/or other components) may be provided in any other suitable arrangements. In the present example, tissue processing system (10) comprises a tissue harvesting device (100) and a console (200). As shown in FIGS. 1-2, tissue harvesting device (100) is configured to removably couple with console (200). In particular, and as will be described in greater detail below, tissue harvesting (100) device is operable to transmit harvested tissue specimens to console (200). Console (200) is then operable to process tissue specimens, and transmit the processed tissue back to tissue harvesting device (100) for subsequent administration to a patient.

As can be best seen in FIG. 1, console (200) of the present example comprises a tissue stirring chamber (300), which is operable to stir tissue transmitted from tissue harvesting device (100). Console (200) further comprises an ultrasonic tissue measuring chamber (400), which receives stirred tissue from tissue stirring chamber (300). If warranted by the size of tissue particles in ultrasonic tissue measuring chamber (400), tissue particles may be communicated to tissue mincing chamber (500), which is in communication with tissue measuring chamber (400), and which may transmit minced tissue back to tissue measuring chamber (400). Tissue particles having a suitable size are ultimately transmitted from tissue measuring chamber (400) to a stimulation chamber (600). Other, undesirable tissue particles are transmitted from tissue measuring chamber (400) to a waste chamber (700). After suitable tissue particles are sufficiently stimulated in stimulation chamber (600), the tissue particles proceed to a fluid removal chamber (800), where at least some fluid is removed from the tissue particles. At this stage, at least some tissue particles may be transmitted to waste chamber (700). In addition or in the alternative, at least some tissue particles may be transmitted to a tissue container (900). In some versions, at least some tissue particles may be transmitted back to tissue harvesting device (100). Fluid removed by fluid removal chamber (800) is transmitted to a fluid reservoir (1000). Fluid reservoir (1000) is also in communication with tissue stirring chamber (300), such that fluid removed by fluid removal chamber (800) may be re-used in a subsequent process of stirring tissue.

Console (200) further includes a fluid pump (1110), which may be used to flush tissue from tissue harvesting device (100) and/or otherwise communicate fluid within system (10). Fluid pump (1110) may comprise a gear pump, peristaltic pump, diaphragm pump, positive displacement pump, or any other suitable type of pump. While fluid pump (1110) is shown as being integrated within console (200), it should be understood that fluid pump (1110) may alternatively be located external to console (200). Furthermore, it should be understood that fluid pump (1110) may be coupled with various other components of console (200), including but not limited to fluid reservoir (1000) (e.g., using fluid reservoir (1000) as a fluid source, etc.).

Tissue may be transported through tissue processing system (10) in a variety of ways. By way of example only, tissue may be transported through at least part of tissue processing system (10) using a vacuum. In addition or in the alternative, tissue may be transported through at least part of tissue processing system (10) using a fluid medium, such as air, saline, a medical fluid component, etc. Such a fluid medium may be pressurized or may be at atmospheric pressure (e.g., providing a pressure differential relative to a vacuum, etc.). In addition or in the alternative, tissue may be transported through at least part of tissue processing system (10) using a pusher, an auger, a conveyor, and/or some other mechanical transport means. As yet another merely illustrative example, tissue may be transported through at least part of tissue processing system (10) using ultrasonic waves or acoustic pressure, such as by activating one or more of the transducers that are described herein as being used for other purposes. As still another merely illustrative example, tissue may be transported through at least part of tissue processing system (10) using magnetic forces (e.g., interacting with an additive in the medical fluid, etc.). It should also be understood that the method and/or apparatus for transporting tissue through tissue processing system (10) may vary based on the location or stage of the tissue within tissue processing system (10). Various other suitable ways in which tissue may be transported through tissue processing system (10) will be apparent to those of ordinary skill in the art in view of the teachings herein.

III. Exemplary Tissue Harvesting Device

As shown in FIGS. 2-3, tissue harvesting device (100) of the present example comprises a body (102) and a needle (110) extending distally from body (102). Needle (110) has a closed tissue piercing tip (112) and a transverse aperture (114) formed proximal to tip (112). A tubular cutter (not shown) is positioned within needle (110) and translates within needle (110) to sever tissue protruding through transverse aperture (114). A vacuum source (not shown) may be positioned within body (102) or external to body (102); and may communicate with needle (110) to draw tissue into transverse aperture (114) when needle (110) is inserted into a patient's tissue. Such a vacuum source may also assist in proximally transporting tissue specimens severed by the cutter to a region within body (102). It should thus be understood that tissue harvesting device (100) may be configured in many ways like a biopsy device. For instance, tissue harvesting device (100) may have various components that are configured and operable in accordance with a MAMMOTOME® biopsy device by Ethicon Endo-Surgery, Inc. of Cincinnati, Ohio and/or in accordance with the teachings of U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2007/0118048, entitled "Remote Thumbwheel for a Surgical Biopsy Device," published May 24, 2007, issued as U.S. Pat. No. 7,442,171; U.S. Pub. No. 2008/0214955, entitled "Presentation of Biopsy Sample by Biopsy Device," published Sep. 4, 2008; U.S. Non-Provisional patent application Ser. No. 12/337,942, entitled "Biopsy Device with Central Thumbwheel," filed Dec. 18, 2008, published as U.S. Pub. No. 2010/0160819; and/or U.S. Non-Provisional patent application Ser. No. 12/483,305, entitled "Tetherless Biopsy Device with Reusable Portion," filed Jun. 12, 2009, issued as U.S. Pat. No. 8,206,316. The disclosure of each of the above-cited U.S. Patents, U.S. Patent Application Publications, and U.S. Non-Provisional Patent Applications is incorporated by reference herein. Of course, tissue harvesting device (100) may have any other suitable components or configurations.

As best seen in FIG. 3, the underside of body (102) in the present example includes a pair of female ports (120, 121) and three recesses (130). Female ports (120, 121) are configured to mate with complementary male ports (220, 221) of console (200); while docking recesses (130) are configured to mate with complementary mounting prongs (230) of console (200). Prongs (230) are configured to fit into recesses (130) and removably secure tissue harvesting device (100) to console (200). Of course, various other types of structures and features may be used to removably secure tissue harvesting device (100) to console (200). By way of example only, such securing features may include snap fits, over-center latches, magnets, clips, clamps, threaded members, etc.

As shown in FIGS. 4A-4B, port (120) includes a seal (122) and an associated conduit (124). A guide chamfer (126) is positioned adjacent to port (120), and is configured to assist in guiding port (220) of console (200) into port (120) of tissue harvesting device (100) as tissue harvesting device (100) is coupled with console (200). As shown in FIG. 4B, seal (122) deforms as port (220) is inserted in port (120), allowing conduit (224) of port (220) to communicate with conduit (124) of port (120). Seal (122) also maintains a seal against port (220) as port (220) is inserted in port (120). In some versions, seal (122) lacks any slit or other type opening therethrough, such that port (220) pierces, tears, or otherwise breaks seal (122) upon insertion of port (220) in port (120). In some other versions, seal (122) includes a preformed slit or other type of feature that is configured to facilitate entry of port (220) through seal (122) while also substantially sealing conduit (124) when port (220) is not inserted in port (120). Seal (122) of the present example is further configured to substantially re-seal conduit (124) when port (220) is decoupled from port (120).

It should be understood that tissue specimens may be communicated from conduit (124) to conduit (224), such that tissue is transported from tissue harvesting device (100) to console via ports (120, 220). For instance, conduit (124) may be in communication with the lumen of a tubular cutter (not shown) and/or a tissue receptacle (not shown) of tissue harvesting device (100); while conduit (224) may be in communication with tissue stirring chamber (300). In some versions, tissue harvesting device (100) performs at least some processing of tissue specimens before the tissue is communicated from port (120) to port (220). For instance, tissue harvesting device (100) may dice, mince, or otherwise reduce the size of tissue specimens obtained by a tubular cutter of tissue harvesting device (100). In addition or in the alternative, tissue harvesting device (100) may mix tissue specimens with a fluid, such that a tissue-fluid mixture is communicated from port (120) to port (220). It should also be understood that ports (121, 221) may have a configuration that is substantially identical to the configuration of ports (121, 221). Furthermore, ports (121, 221) may be used to communicate processed tissue, saline, and/or medical fluid components from console (200) to tissue harvesting device (100). For instance, port (221) may be in communication with fluid removal chamber (800) and fluid pump (1110) of console (200); while port (121) may ultimately be in communication with needle (110).

To the extent that tissue harvesting device (100) is used to apply processed tissue and/or medical fluid components from console (200) to a site in a patient, needle (110) may be used in some versions. For instance, the processed tissue and/or medical fluid components may be dispensed through transverse aperture (114). In addition or in the alternative, a dispensing needle (150) may be used. Dispensing needle (150) of the present example has an open distal end (152). Body (102) is configured to selectively receive either type of needle (110, 150). For instance, needle (110) may be removed from body (102) an dispensing needle (150) may then be coupled with body (102). Dispensing needle (150) may be used to administer processed tissue and/or medical fluid components from console (200) to a site in a patient. In addition or in the alternative, dispensing needle (150) may be used to deposit processed tissue and/or medical fluid components from console (200) into another container. As yet another variation, a separate tissue therapy device (101) may be coupled with console (200) in a manner similar to tissue harvesting device (100). Tissue therapy device (101) may include a body (103) and a distally extending needle (111) having an open distal end (115) that is configured to dispense processed tissue and/or medical fluid components at a target site in a patient.

Still other suitable components, features, configurations, and operabilities for tissue harvesting device (100) will be apparent to those of ordinary skill in the art in view of the teachings herein.

IV. Exemplary Tissue Processing Console

A. Overview

Figure 5:
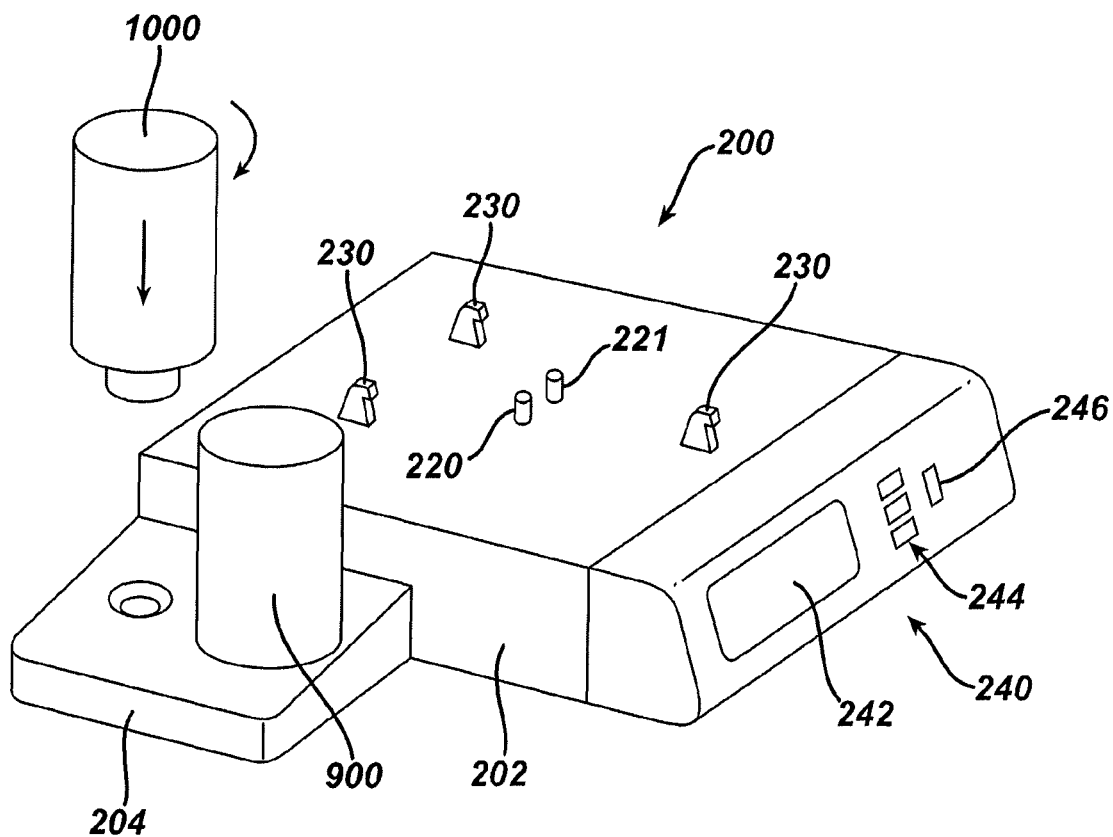
FIG. 5 depicts a perspective view of an exemplary console of the tissue processing system of FIG. 1.

Tissue processing console (200) of the present example comprises a housing (202) and a control panel (240) as shown in FIG. 5. Control panel (240) of this example includes a display (242), a plurality of buttons (244), and an input/output port (246). Display (242) is operable to render information to the user about the status of tissue processing system (10), such as whether processed tissue is ready for use, which stage of the process tissue is in, what the tissue particle size is, how many tissue particles there are, how much tissue had to be sent to waste chamber (700), how much fluid is in fluid reservoir (1000), etc. By way of example only, display (242) may comprise a plurality of LEDs, a textual display, a graphical user interface, a touch screen interface, and/or a variety of other types of display technologies. Buttons (244) may comprise electromechanical switches, thin film switches, capacitive switches, and/or various other features configured to receive user input. In some versions where display (242) comprises a touch screen, buttons (244) are omitted. Of course, buttons (244) may be omitted if desired, even if display (242) does not comprise a touch screen or even if display (242) is also omitted. Input/output port (246) of the present example comprises a USB port, though any other suitable type of input/output port (246) may be used. Furthermore, it should be understood that console (200) may include a plurality of input/output ports (246) if desired; or even no input/output ports (246) if desired. In the present example, input/output port (246) may be coupled with a keyboard, mouse, flash drive, external hard drive, monitor, and/or a computer. Thus, console (200) may receive data and/or commands, etc. via input/output port (246). Similarly, console (200) may transmit data and/or commands, etc. via input/output port (246).

Figure 6:
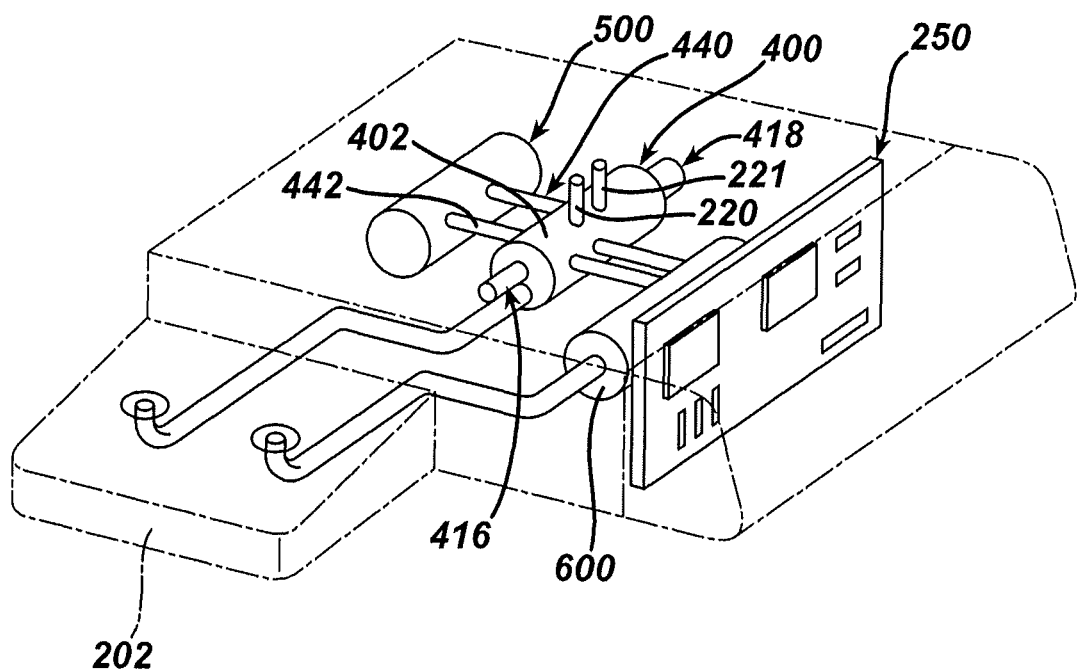
FIG. 6 depicts a perspective view of exemplary tissue processing components of the console of FIG. 5, with the console housing shown in broken lines.

Control panel (240) is in communication with control circuitry (250), which is shown in FIG. 6. Control circuitry (250) is also in communication with various other components (300, 400, 500, 600, 800, 1110) within console (200). In particular, control circuitry (250) is configured to control such components (300, 400, 500, 600, 800, 1110) in accordance with user inputs via control panel (240) and/or in accordance with predefined control algorithms or routines. It should be understood that control circuitry (250) may include various types of components, including but not limited to one or more processors and one or more memory devices. Various suitable ways in which control circuitry (250) may be configured will be apparent to those of ordinary skill in the art in view of the teachings herein.

B. Exemplary Coupling of Tissue Harvesting Device with Console

In the present example, and as noted above, console (200) is configured to provide a saline flush of tissue harvesting device (100) when tissue harvesting device (100) is coupled with console (200). In particular, fluid pump (1110) is operable to force saline through ports (121, 221). Such flushing may urge tissue specimens from within tissue harvesting device (100) into tissue stirring chamber (300) via ports (120, 220). Saline that was forced through ports (121, 221) may likewise be communicated back to console (200) via ports (120, 220). In some versions, such flushing is automatically provided as soon as tissue harvesting device (100) is coupled with console (200). For instance, tissue harvesting device (100) may be configured to actuate a trigger (e.g., mechanically, such as by pushing; electronically, such as by an RFID tag or EAS tag, etc) in console (200) as soon as tissue harvesting device (100) is coupled with console (200). Alternatively, console (200) may require a user to manually activate a button (244) or provide some other form of input in order to initiate a flushing cycle. It should also be understood that a manual input for saline flush may be disabled until tissue harvesting device (100) is coupled with console (200). In some versions, tissue harvesting device (100) is configured to communicate information to console (200) (e.g., via wire, wirelessly, via metal contacts, etc.) indicating the total number of tissue specimens and/or other tissue specimen information; and console (200) may automatically adjust the amount of saline communicated by fluid pump (1110) to provide a predefined solid/fluid ratio. As yet another merely illustrative variation, fluid pump (1110) may be provided in tissue harvesting device (100) instead of being provided in console (200). Of course, such saline flushing is merely optional, and may be modified or even omitted as desired.

Once a desired amount of tissue specimens have been communicated from tissue harvesting device (100) to console (200), tissue harvesting device (100) may be removed from console (200). Tissue harvesting device (100) may then be used to harvest additional tissue specimens. Alternatively, tissue harvesting device (100) may simply be set aside. As another alternative, tissue harvesting device (100) may remain coupled with console (200) at this stage if desired. In still other versions, some or all of the components and/or functionalities of console (200) are integrated into tissue harvesting device (100), such that a separate console (200) lacks at least some such components or is even omitted altogether.

C. Exemplary Stirring Chamber

Figure 10:
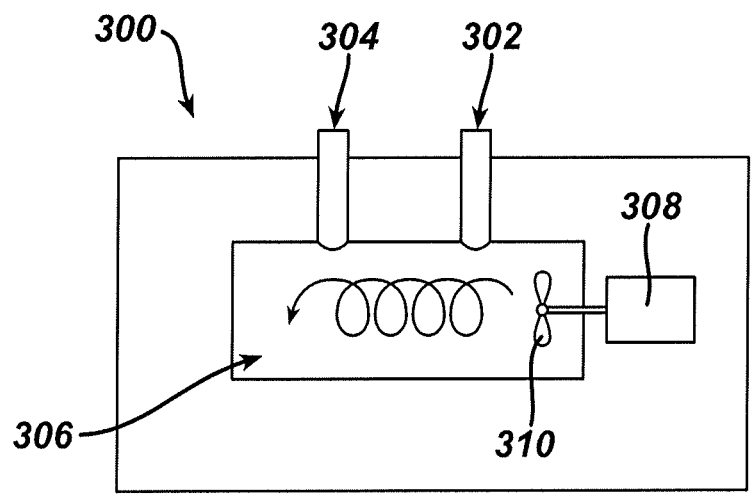
FIG. 10 depicts a side cross-sectional view of an exemplary stirring chamber of the console of FIG. 5.

As noted above, port (220) is in communication with a stirring chamber (300) in the present example. Stirring chamber (300) is operable to stir tissue communicated from tissue harvesting device (100) with a fluid medium, such as saline and/or a medical fluid component, etc., to disperse the tissue within the fluid medium. A shown in FIG. 10, stirring chamber (300) comprises an input port (302), an output port (304), and a reservoir (306). A mixing blade (310) is positioned in reservoir (306), and is rotated by a corresponding motor (308) to mix tissue and a fluid medium within reservoir (306). Motor (308) may be selectively activated by control circuitry (250). While motor (308) and blade (310) are used to mix tissue and a fluid medium in the present example, it should be understood that various other structures and techniques may be used to mix tissue and a fluid medium. For instance, motor (308) may rotate various other types of structures instead of rotating a blade (310). As another variation, a solenoid or other type of device may reciprocate an agitating member within reservoir (306). As additional merely illustrative variations, stirring chamber (300) may use ultrasonic vibration or electrohydrodynamics (EHD) to mix tissue with a fluid medium. Other suitable ways in which stirring chamber (300) may mix tissue and a fluid medium will be apparent to those of ordinary skill in the art in view of the teachings herein. Tissue and a fluid medium may be held and mixed in reservoir (306) for any suitable duration. It should also be understood that one or more stirring chambers (300) may be located elsewhere in system (10), in addition to or in lieu of being located in the fluid path between tissue harvesting device and ultrasonic tissue measuring chamber (400). Of course, as with other components described herein, stirring chamber (300) may simply be omitted altogether if desired.

D. Exemplary Tissue Measuring Chamber

Figure 7:
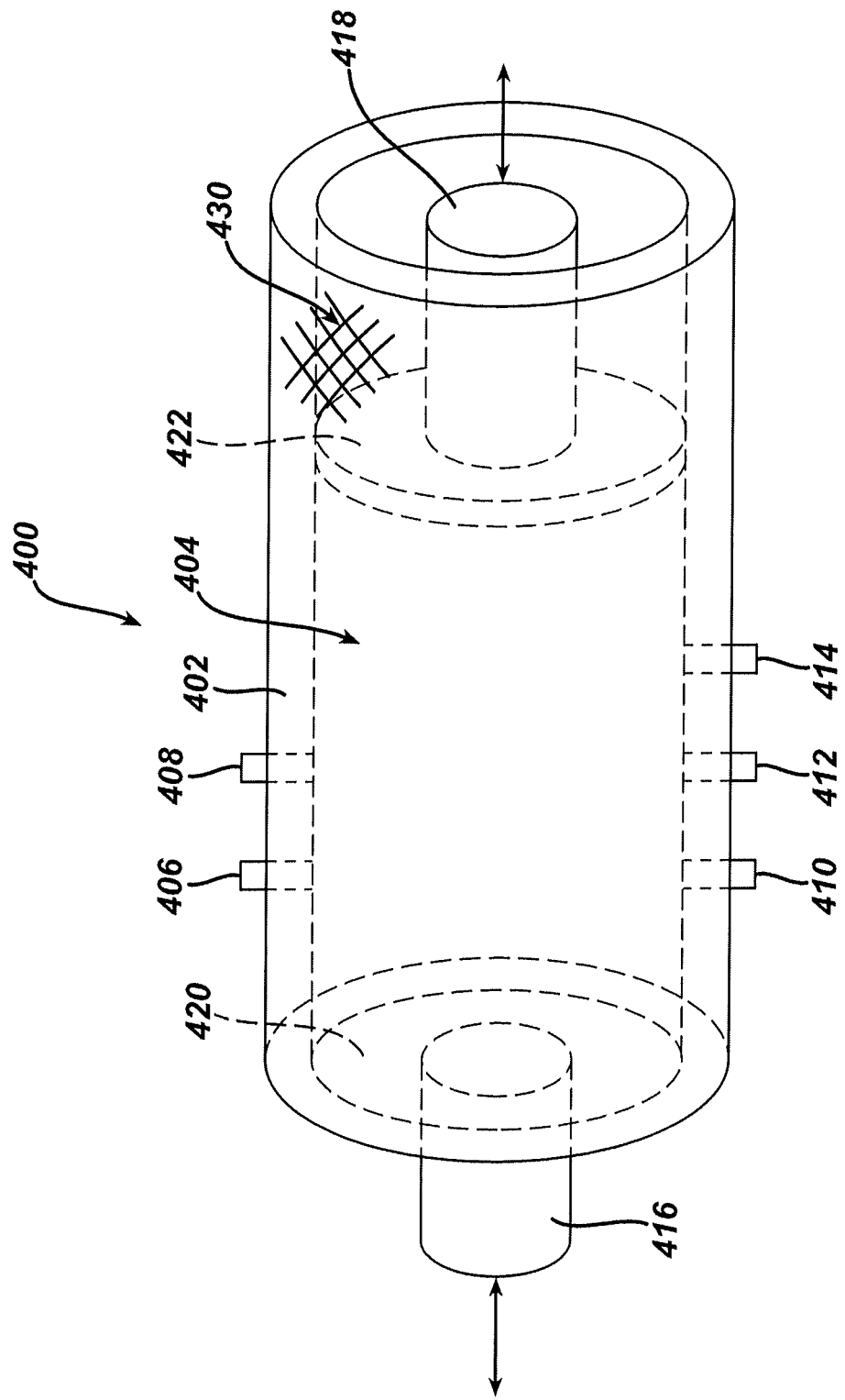
FIG. 7 depicts a perspective view of an exemplary ultrasonic tissue measuring chamber of the console of FIG. 5.

In the present example, after being stirred within stirring chamber (300), the tissue/fluid mixture is transmitted to ultrasonic tissue measuring chamber (400). An example of ultrasonic measuring chamber (400) is shown in FIG. 7. It should also be noted that FIG. 6 shows a variation in which port (220) is directly coupled with tissue measuring chamber (400), such that a separate stirring chamber (300) is omitted in the version shown in FIG. 6. In the present example, tissue measuring chamber (400) comprises a housing (402) that defines a reservoir (404). A pair of input ports (406, 408) and three output ports (410, 412, 414) are in fluid communication with reservoir (404). Input port (406) is configured to communicate a tissue/fluid mixture from stirring chamber (300) into reservoir (404). Input port (408) is configured to communicate a tissue/fluid mixture from mincing chamber (500) into reservoir (404). Output port (410) is configured to communicate tissue from reservoir (404) to waste chamber (700). Output port (412) is configured to communicate a tissue/fluid mixture from reservoir (404) to mincing chamber (500). Outlet port (414) is configured to communicate tissue from reservoir (404) to stimulation chamber (600). Examples of these types of communication to and from reservoir (404) will be described in greater detail below.

Tissue measuring chamber (400) further comprises a drive transducer (416) and a receiving transducer (418). Drive transducer (416) is secured to fixed plunger (420), which is secured to housing (402). Receiving transducer (418) is secured to a movable plunger (422), which is movable relative housing (402). In particular, movable plunger (422) is translatable along the axis defined by housing (402). It should be understood that plunger (420) may be movable relative to housing (402) in some versions, in addition to or in lieu of plunger (422) being movable relative to housing (402). In addition, it should be understood that plunger (422) may be fixed relative to housing (402) in some versions, in addition to or in lieu of plunger (420) being fixed relative to housing (402). Transducers (416, 418) are each in communication with control circuitry (250). Drive transducer (416) is configured to convert electrical energy into vibrational energy. In particular, drive transducer (416) is operable to generate ultrasonic energy by vibrating at ultrasonic frequencies in response to control signals from control circuitry (250). For instance, drive transducer (416) may operate within parameters as taught in U.S. Pub. No. 2009/0051350, the disclosure of which is incorporated by reference herein. As another merely illustrative example, drive transducer (416) may operate within parameters as taught in "Measuring Bubble, propand Particle Sizes in Multiphase Systems with Ultrasound" by Cents Brilman and Versteeg (AIChE Journal, November 2004, Volume 50, Number 11, pp 2750-2762), the disclosure of which is incorporated by reference herein. Alternatively, drive transducer (416) may operate at any other suitable frequencies, amplitudes, and/or full resonant wavelengths, etc. It should also be understood that it may not be necessary for drive transducer (416) to achieve resonance in all examples of use.

Drive transducer (416) may comprise an endmass, a plurality of piezoelectric discs, and a horn that is oriented toward reservoir (404). The piezoelectric discs may comprise lead zirconate titanate (PZT) and/or any other suitable material or combination of materials. The horn may be formed of Ti64, though it should be understood that any other suitable material(s) may be used. Electrical energy is provided to the endmass from control circuitry (250). This excites the piezo discs to produce the ultrasonic vibrational energy, which is communicated to the horn. The horn acoustically amplifies the ultrasonic wave, such that the configuration of the horn provides acoustic gain. An acoustic lens may be included, if desired. It should be understood that, to the extent that drive transducer (416) includes more than one piezoelectric element (e.g., crystals), such piezoelectric elements may be provided in any suitable arrangement (e.g., stacked and/or arrayed, etc.). It should also be understood that drive transducer (416) may be configured as a diagnostic transducer (e.g., relatively high frequency and relatively low energy) rather than being configured as a power transducer (e.g., relatively low frequency and relatively high energy), though a HIFU type of transducer may be used if desired. By way of example only, drive transducer (416) may be configured in accordance with the teachings of any one or more of following, each of which is incorporated by reference herein: U.S. Pub. No. 2008/0294054, entitled "Ultrasound Probe and Diagnostic Ultrasound System," published Nov. 27, 2008; U.S. Pub. No. 2009/0034370, entitled "Diagnostic Ultrasound Transducer," published Feb. 5, 2009; U.S. Pat. No. 5,823,962, entitled "Ultrasound Transducer for Diagnostic and Therapeutic Use," issued Oct. 20, 1998; and/or U.S. Pat. No. 6,489,706, entitled "Medical Diagnostic Ultrasound Transducer and Method of Manufacture," issued Dec. 3, 2002. Various other suitable ways in which drive transducer (416) may be configured will be apparent to those of ordinary skill in the art in view of the teachings herein.

Receiving transducer (418) of the present example is essentially identical in construction to drive transducer (416). Receiving transducer (418) may thus be configured to absorb and sense ultrasonic energy that is passed through the tissue/fluid mixture, with control circuitry (250) being configured to calculate the size of tissue particles within reservoir (404) based at least in part on ultrasonic energy absorbed by receiving transducer (418). Of course, receiving transducer (418) may have any other suitable alternative configuration as will be apparent to those of ordinary skill in the art in view of the teachings herein. It should also be understood that receiving transducer (418) may even be omitted in some versions. For instance, receiving transducer (418) may be omitted in some versions where measurement of tissue particle size is done through reflection of the ultrasonic energy. In some such versions, drive transducer (416) may be used to sense the reflected ultrasonic energy, with control circuitry (250) being configured to calculate the size of tissue particles within reservoir (404) based at least in part on reflected ultrasonic energy absorbed by drive transducer (416). Of course, tissue particle size may also be measured based on a combination of ultrasonic energy absorbed by drive transducer (416) and receiving transducer (418); and/or in any other suitable fashion.

Figure 9:
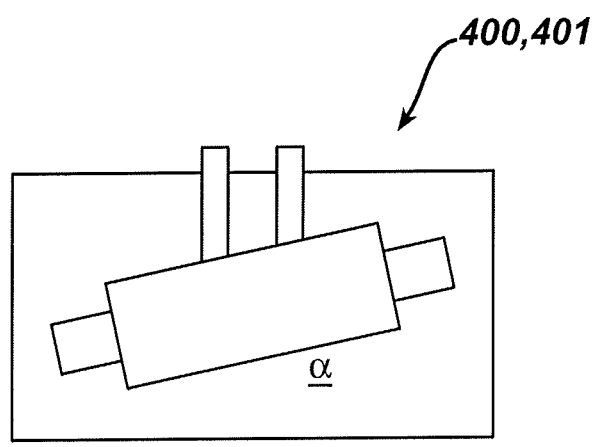
FIG. 9 depicts a side view of an ultrasonic tissue measuring chamber mounted at a non-horizontal angle.

In the present example, drive transducer (416) operates at parameters selected to de-aerate the tissue/fluid mixture in reservoir (404), such that drive transducer (416) removes entrained air from the tissue/fluid mixture. For instance, power applied to drive transducer (416) may be increased to provide ultrasonic de-aeration in some settings. In some versions, housing (402) is configured or oriented such that reservoir (404) is oriented along a non-horizontal axis, allowing air to collect at a longitudinal end of reservoir (404) for subsequent removal (e.g., by active withdrawal or passive venting, etc.). For instance, FIG. 9 shows housing (402) oriented at a non-horizontal angle α. In addition, movable plunger (422) is moved within housing (402) in the present example to modify the volume of reservoir (404) based on the volume of tissue and/or fluid communicated through input (406) into reservoir (404). In addition, movable plunger (422) is movable to expose a tissue/fluid mixture within reservoir (404) to an absorbent medium (430), which is configured to remove fluid from the tissue/fluid mixture in reservoir (404).

Absorbent medium (430) may be formed of any suitable material, including but not limited to various paper compositions, cotton, various materials found in tampons or diapers, etc. Alternatively, absorbent medium (430) may be formed of any other suitable material or combination of materials. In some versions, rather than moving plunger (422) to expose the tissue/fluid mixture to absorbent medium (430) with plunger (420) staying in a fixed position, plungers (420, 422) move together relative to housing (402) to expose the tissue/fluid mixture to absorbent medium (430). In other words, plungers (420, 422) may move together in some versions to essentially shift the location of reservoir (404) within housing without changing the volume of reservoir (404) to expose the tissue/fluid mixture to absorbent medium (430). In any case, movement of one or both of plungers (420, 422) may be accomplished in various ways, including but not limited to using one or more drive motors, solenoids, pneumatic actuators, hydraulic actuators, etc.

Once the tissue/fluid mixture in reservoir (404) has been de-aerated, control circuitry (250) may begin to operate drive transducer (416) in a second operational mode. In particular, control circuitry (250) may activate drive transducer (416) to emit ultrasonic energy configured to measure the size of tissue particles in the tissue/fluid mixture when drive transducer (416) is operated in the second operational mode. In some versions, such tissue particle size measurement may be provided in accordance with the teachings of "Measuring Bubble, propand Particle Sizes in Multiphase Systems with Ultrasound" by Cents Brilman and Versteeg (AIChE Journal, November 2004, Volume 50, Number 11, pp 2750-2762), the disclosure of which is incorporated by reference herein. For instance, control circuitry (250) may apply a drive signal to drive transducer (416) to emit ultrasonic energy that passes through the tissue/fluid mixture and ultimately reaches receiving transducer (418). Such emissions by drive transducer (416) may include frequency sweeps and/or amplitude sweeps within any suitable range or ranges. Receiving transducer (418) is also in communication with control circuitry (250), which includes a logic configured to process data obtained through receiving transducer (418). In particular, control circuitry (250) may measure the velocity profile and/or the attenuation profile of the ultrasound energy received by receiving transducer (418), which may then be interpreted by control circuitry (250) to indicate the size of tissue particles in reservoir (404). As another merely illustrative example, tissue measuring chamber (400) and control circuitry (250) may be configured to measure the size of tissue particles in reservoir (404) in accordance with the teachings of U.S. Pub. No. 2009/0051350, entitled "Device and Process for Detecting Particles in a Flowing Liquid," published Feb. 26, 2009, the disclosure of which is incorporated by reference herein. As yet another merely illustrative example, drive transducer (416) and/or some other transducer positioned at the same end of reservoir (404) as drive transducer (416) may be configured to receive ultrasonic pulses reflected back from tissue particles in reservoir (404), and signals indicative of such reflected pulses may be processed by control circuitry (250) to determine the tissue particle size.

Regardless of how the tissue particle sizes are measured, control circuitry (250) may compare the measured tissue particle sizes to a predetermined size range to determine whether the size of tissue particles in reservoir (404) falls within the predetermined size range. For instance, the predetermined size range may be between approximately 0.5 $mm^3$ and approximately 2 $mm^3$; or more particularly between approximately 0.5 $mm^3$ and approximately 0.75 $mm^3$. It should be understood that the predetermined size range may be a set range originally programmed in memory of control circuitry (250); or the size range may be established by a user by input through control panel (240). To the extent that console (200) allows a user to establish the size range, this may be provided in various ways. In some versions, control panel (240) allows a user to select a size range from various predetermined size ranges. In addition or in the alternative, control panel (240) may allow the user to manually input a customized size range. Various suitable tissue particle size ranges and methods for establishing such ranges will be apparent to those of ordinary skill in the art in view of the teachings herein.

As part of a routine of processing tissue particle measurements sensed by receiving transducer (418), sensed by drive transducer (416), and/or otherwise sensed, control circuitry (250) may also provide a process for transferring tissue particles based on their size. For instance, in some versions, control circuitry (250) is configured to provide transmission of tissue particles whose size is above the predetermined range from tissue measuring chamber (400) to mincing chamber (500) via output port (412); to provide transmission of tissue particles whose size is below the predetermined range from tissue measuring chamber (400) to waste chamber (700) via output port (410); and to provide transmission of tissue particles whose size is within the predetermined range from tissue measuring chamber (400) to stimulation chamber (600) via outlet port (414). In some versions, such transmission is accomplished in part through activation of fluid pump (1100). In addition, it should be understood that each outlet port (410, 412, 414) may include a respective valve that is selectively opened by control circuitry (250), such as by activating a solenoid or other device associated with a given valve. Processing of tissue particles in mincing chamber (500) and in stimulation chamber (600) will be described in greater detail below. Tissue particles that are transmitted from reservoir (404) to waste chamber (700) via output port (410) may simply be disposed of or otherwise dealt with.

In addition to or in lieu of using fluid pump (1100) to transmit tissue particles from tissue measuring chamber (400) to mincing chamber (500), stimulation chamber (600), or waste chamber (700), drive transducer (416) may be used to transmit tissue particles. For instance, drive transducer (416) may be tuned to create a DC force in tissue particles and/or an acoustic pressure that is operable to drive tissue particles toward one or more of output ports (410, 412, 414). In some versions, the tissue particles will move against or with the radiation force from drive transducer (416) based on the size of the tissue particles. The radiation force may be controlled by amplitude and/or based on one or more other operating parameters. The waveform may be pulsed to advance the tissue particles from node to node in some versions. In addition or in the alternative, at least some degree of frequency modulation may facilitate movement of tissue particles.

In some versions, drive transducer (416) may be tuned and selectively activated to move small tissue particles first (e.g., toward waste chamber (700)), then move large tissue particles second (e.g., toward mincing chamber (500)), then move medium sized tissue particles third (e.g., toward stimulation chamber (600)). For instance, ultrasonic energy emitted at a first amplitude may move tissue particles whose size is less than a predetermined size range away from drive transducer (416) toward output port (410). Ultrasonic energy emitted at a second amplitude (e.g., higher than the first amplitude) may move tissue particles whose size falls within the predetermined size range away from drive transducer (416) toward output port (414). Ultrasonic energy emitted at a third amplitude (e.g., higher than the second amplitude) may move tissue particles whose size exceeds the predetermined size range away from drive transducer (416) toward output port (412). Drive transducer (416) may successively cycle through all three amplitudes, operating at a particular amplitude (or within particular amplitude ranges) for any suitable time period. By way of example only, drive transducer (416) may be operated in accordance with the teachings of "Moving Particles with Ultrasonic Standing Waves" by Martin McDonnell (DSTL Codex Journal, Summer 2008, Issue 1, pp. 1-4), the disclosure of which is incorporated by reference herein, to move tissue particles. Alternatively, drive transducer (416) may be used to move tissue particles in any other suitable fashion, as will be apparent to those of ordinary skill in the art in view of the teachings herein.

It should also be understood that measuring chamber (400) may have only one output port in some versions. For instance, a routing apparatus (not shown) may be coupled with the single output port, and may route output from measuring chamber (400) to a selected destination (e.g., mincing chamber (500), waste chamber (700), or stimulation chamber (600), etc.) based on instructions from control circuitry (250).

Before tissue particles are transferred from reservoir to mincing chamber (500), the tissue particles may be separated from their carrier fluid to some degree. In the present example, once it is determined that reservoir (404) contains tissue particles that are within the predetermined size range, plunger (422) is moved relative to housing to expose absorbent medium (430) to the fluid carrier within reservoir (404). Absorbent medium (430) may then absorb at least some of the fluid carrier. To assist in this process, plunger (420) may also move within housing (402) toward plunger (422), to compress the fluid carrier and thereby urge the fluid carrier into absorbent medium (430). To the extent that either plunger (420, 422) translates within housing (402), such translation may be to a predetermined position or to a position calculated by control circuitry (250) based on any suitable factor or factors such as the volume of tissue/fluid introduced into reservoir (404), the final number of tissue particles or cells in reservoir (404), and/or based on any other suitable factor or combination of factors. With the fluid carrier being absorbed by absorbent medium (430), the tissue cells would remain within reservoir (404). If desired, the absence of fluid in reservoir (404) may be sensed in various ways. For instance, the absence of fluid in reservoir (404) may be sensed based on the pressure on either or both transducers (416, 418), based on the torque on a motor used to push on one of transducers (416, 418), based on backloading on a solenoid used to push one of transducers (416, 418), based on feedback from a capacitance sensor or other type of hydrosensitive sensor, and/or in any other suitable fashion. It should also be understood that any or all of output ports (410, 412, 414) may be positioned near or adjacent to absorbent medium (430), which may facilitate communication of tissue through output ports (410, 412, 414) after fluid has been substantially removed from a tissue/fluid mixture by absorbent medium (430). Furthermore, some fluid may be kept in reservoir (404) despite the use of absorbent medium (430), with such residual fluid being used to facilitate conveyance of tissue particles to and through one or more of output ports (410, 412, 414). To the extent that all fluid has been removed from reservoir (404), tissue particles may be conveyed to and through one or more of output ports (410; 412, 414) using a plunger and/or some other feature, structure, device, or technique, etc. In some versions, tissue is removed manually from reservoir (404) after the tissue has been separated from fluid, such as by opening a lid or retrieving the tissue through an access port, etc.

In some other versions, the interior wall of housing (402) is lined with an absorbent medium (not shown), which is covered by a sleeve (not shown) during the process of measuring tissue particle size, etc. Once it is determined that reservoir (404) contains tissue particles that are within the predetermined size range, the sleeve may be removed to expose the absorbent medium to the fluid carrier. The absorbent medium may then absorb at least some of the fluid carrier. To the extent that the absorbent medium is porous, the pore size of the absorbent medium may be selected to reduce or even avoid tissue particles getting stuck in the pores of the absorbent medium. As another merely illustrative example, a tissue/fluid mixture may be passed through a screen or other type of filter that is configured to catch tissue particles while allowing the fluid to pass through. In some versions, regardless of how tissue particle size is measured and regardless of how/whether fluid is removed after particle size measurement, reservoir (404) may be flushed with a fluid such as saline.

Figure 8:
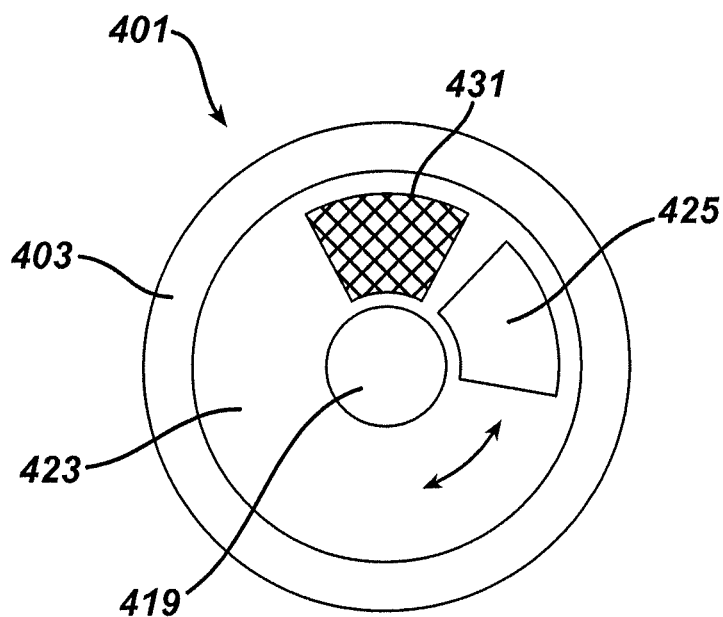
FIG. 8 depicts an end view of an exemplary alternative ultrasonic tissue measuring chamber of the console of FIG. 5

An exemplary alternative tissue measurement chamber (401) is shown in FIG. 8. In this example, an absorbent medium (431) at least partially encircles a receiving transducer (419). In addition, absorbent medium (431) forms part of plunger (423), which is movable relative to housing (403) in this example. A cover member (not shown) may selectively cover absorbent medium (431) within the reservoir defined by housing (403). This cover member may be moved to expose absorbent medium (431) at the appropriate time, to allow absorbent medium (431) to absorb at least some of the fluid carrier in the reservoir. A relief mechanism (425) is also provided in plunger (423) in this example. Relief mechanism (425) is operable to prevent material from leaking out of tissue measurement chamber (401) until relief mechanism (425) is opened to allow fluid to be drained from tissue measurement chamber (401). In some versions, relief mechanism (425) is used to remove substantially all of the fluid, while absorbent medium (431) is used to soak up any remaining fluid. Tissue measurement chamber (401) may otherwise be configured like tissue measurement chamber (400) as described above; or may have any other suitable configuration.

Figure 11:
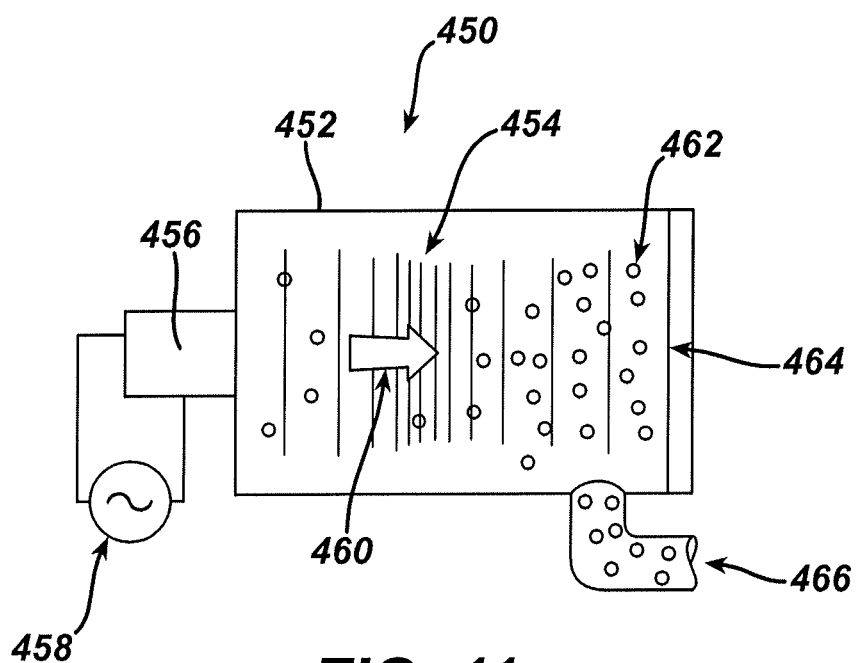
FIG. 11 depicts a schematic view of another exemplary alternative ultrasonic tissue measuring chamber of the console of FIG. 5.

Another exemplary alternative tissue measurement chamber (450) is shown in FIG. 11. In this example, tissue measuring chamber (450) comprises a housing (452) defining a reservoir (454). A drive transducer (456) is positioned at one end of housing (452). A sinusoidal signal (458) is applied to drive transducer (456) to create an acoustic pressure (460) that drives solid cellular material (462) toward the opposite end of reservoir (454). This opposite end of reservoir (454) may include a solid reflecting or absorbing surface (464). In some versions, the sinusoidal signal (458) is continuous. As another example, the sinusoidal signal (458) may be pulsed. As yet another example, the sinusoidal signal (458) may be frequency modulated. As still another example, the sinusoidal signal (458) may be amplitude modulated. Of course, the sinusoidal signal (458) may have any suitable combination of such properties, if desired. Solid cellular material (462) that is sized within the selected tissue particle material range is then communicated through output port (466) and is further processed in accordance with the teachings herein. It should therefore be understood that tissue measurement chamber (450) may have other components, features, and operabilities as described above in the context of tissue measurement chamber (400) and/or tissue measurement chamber (401).

In some versions, a single chamber is used to both stir a tissue/fluid mixture and perform ultrasonic tissue measuring. For instance, the same ultrasonic field that de-aerates a tissue/fluid mixture may also effectively stir the tissue/fluid mixture.

As another merely illustrative example, drive transducer (416) may be activated to emit a quick pulse of high intensity ultrasound to help mix tissue particles in a fluid solution. Thus, it should be understood that components, features, and/or functionalities of stirring chamber (300) may be incorporated into ultrasonic tissue measuring chamber (400). Similarly, components, features, and/or functionalities of ultrasonic tissue measuring chamber (400) may be incorporated into tissue stirring chamber (300). Various suitable ways in which such integration may be accomplished will be apparent to those of ordinary skill in the art in view of the teachings herein.

While tissue measuring chamber (400) uses ultrasound to measure tissue particle sizes, it should be understood that various other types of methods may be used to measure tissue particle sizes. By way of example only, tissue measuring chamber (400) may use an electric field, laser diffraction, and/or various other techniques to detect tissue particle size as will be apparent to those of ordinary skill in the art in view of the teachings herein. It should also be understood that, with an understanding of tissue particle size as sensed by tissue measuring chamber (400), and with an understanding of the total volume of tissue (e.g., based on location of plungers (420, 422), the total number of tissue particles may be estimated, if desired.

E. Exemplary Tissue Mincing Chamber

The following discussion will be provided in the context of tissue measuring chamber (400), though it should be understood that the following may equally apply in versions where tissue measuring chamber is substituted with tissue measuring chamber (401) or tissue measuring chamber (450). As noted above, upon processing tissue particle measurements sensed by receiving transducer (418) or otherwise sensed, control circuitry (250) is configured to provide transmission of tissue particles whose size is above the predetermined range from reservoir (404) to mincing chamber (500) via output port (412). As shown in FIG. 6, output (412) of measuring chamber (400) is coupled with mincing chamber (500) via a tube (440); while input (408) of measuring chamber (400) is coupled with mincing chamber (500) via a tube (442). Of course, chambers (400, 500) may be in fluid communication with each other in any other suitable fashion.

Mincing chamber (500) is operable to mince the tissue particles into smaller pieces; then transmit the minced tissue particles back to reservoir via input port (408). Mincing chamber (500) may include various types of components that are operable to mince tissue particles. By way of example only, mincing chamber (500) may include one or more movable mincing blades, one or more mincing screens or grids, one or more grinding wheels, one or more ultrasonic mincing transducers, and/or any other suitable components, features, or devices that are operable to mince tissue particles. In some versions where mincing chamber (500) ultrasonically minces tissue, mincing chamber (500) may include a sieve or other type of structure that vibrates ultrasonically, such that tissue is minced as it passes through the sieve or other type of vibrating structure. By way of example only, an ultrasonic mincing sieve may comprise three to five parallel blades that ultrasonically vibrate simultaneously. Other suitable ways in which an ultrasonic sieve or other type of ultrasonic mincing device may be configured will be apparent to those of ordinary skill in the art in view of the teachings herein. To the extent that mincing chamber (500) includes one or more mincing members that are subject to selective activation, it should be understood that control circuitry (250) may be configured to provide such selective activation. As another merely illustrative example, mincing chamber (500) may include a manually movable mincing member, such that the mincing member is actuated by a user manually manipulating a handle, crank, dial, or other type of manual driving input.

In some versions, the data indicating the size of tissue particles measured in reservoir (404) is used to influence operation of mincing chamber (500). That is, control circuitry (250) may select a length and/or intensity of time tissue spends in mincing chamber (500) based on the size of the tissue particles that was originally measured in reservoir (404). For instance, if control circuitry (250) determines that tissue particles in reservoir (404) are significantly larger in size than the acceptable size range, control circuitry (250) may activate mincing chamber (500) to mince the tissue for a significant length of time and/or at a significantly high intensity. If control circuitry (250) determines that tissue particles in reservoir (404) are slightly larger in size than the acceptable size range, control circuitry (250) may activate mincing chamber (500) to mince the tissue for a relatively short length of time and/or at a relatively low intensity. Other various ways in which the measured size of tissue particles may be used to influence operation of mincing chamber (500) will be apparent to those of ordinary skill in the art in view of the teachings herein.

Once mincing chamber (500) has completed at least one cycle of mincing tissue, the minced tissue may be communicated back to measuring chamber (400) via input port (408). As with other instances of tissue transport described herein, such transmission may be carried out using fluid pump (1100) and/or various other types of transport means. Similarly, a valve at port (408) may be selectively opened while a valve at port (412) may be selectively closed when tissue is transmitted from mincing chamber (500) back to measuring chamber (400). In some other versions, a single port provides bi-directional communication between chambers (400, 500). Once the minced tissue reaches reservoir (404), measuring chamber (400) and control circuitry (250) may then re-measure the minced tissue and compare the minced tissue particle size to the predetermined size range as described above. Based on this comparison, the minced tissue may be further processed as described above. It should therefore be understood that tissue may be recycled through mincing chamber (500) as many times as needed until the tissue particles reach a size falling within the predetermined range.

It should be noted that a mincing chamber (500) may be located "upstream" of measuring chamber (400) in some versions, if desired, particularly if tissue harvesting device (100) is configured to obtain relatively large tissue specimens that are expected to initially be larger than the predetermined size range. Such an upstream mincing chamber (500) may be provided in addition to or in lieu of a mincing chamber (500) that receives tissue after the tissue passes through measuring chamber (400) as described above. It should also be understood that, in versions where a mincing chamber (500) is provided upstream of a measuring chamber (400), tissue may be communicated back to mincing chamber (500) from measuring chamber (400) in the event that the tissue particles are found to exceed the predetermined size range as described above.

It should also be understood that a single chamber may be used to perform both ultrasonic tissue measuring and tissue mincing (ultrasonic or otherwise) in some versions. Thus, it should be understood that components, features, and/or functionalities of ultrasonic tissue measuring chamber (400) may be incorporated into tissue mincing chamber (500). Likewise, components, features, and/or functionalities of tissue mincing chamber (500) may be incorporated into ultrasonic tissue measuring chamber (400). Various suitable ways in which such integration may be accomplished will be apparent to those of ordinary skill in the art in view of the teachings herein. Similarly, various other suitable ways in which tissue mincing chamber (500) may be configured an operated, regardless of whether tissue mincing chamber (500) and tissue measuring chamber (400) are combined, will be apparent to those of ordinary skill in the art in view of the teachings herein.

F. Exemplary Tissue Stimulation Chamber

As noted above, upon processing tissue particle measurements sensed by receiving transducer (418) or otherwise sensed, control circuitry (250) is configured to provide transmission of tissue particles whose size is within the predetermined range from reservoir (404) to stimulation chamber (600) via output port (414). Stimulation chamber (600) is operable to electrically stimulate the tissue particles. In some versions, stimulation chamber (600) is formed at least in part of poly(dimethylsiloxane) (PDMS) on glass. Of course, any other suitable material or combination of materials may be used. Also in some versions, stimulation chamber (600) is formed using a combined process including stereolithography and mold curing, though it should be understood that any other suitable process or combination of processes may be used. While stimulation chamber (600) of the present example comprises just one chamber or well for stimulating tissue, it should be understood that stimulation chamber (600) may have any other suitable number of chambers or wells (e.g., two, four, etc.) provided in an array or in any other suitable configuration. Stimulation chamber (600) includes a pair of interior electrodes (not shown), which are provided at opposite sides of each inner chamber or well defined by stimulation chamber (600). Control circuitry (250) is operable to activate the electrodes to provide electrical stimulation to tissue cells that are introduced into stimulation chamber (600). Such electrical stimulation may increase the effectiveness of tissue cells in their subsequent use. For instance, electrical stimulation may increase stem cell activity. It should also be understood that the current used to keep the voltage in stimulation chamber (600) substantially constant could also be used as a means to approximate the total mass of cells within stimulation chamber (600).

As another merely illustrative example, control circuitry (250) may be configured to stimulate the electrodes of stimulation chamber (600) with square wave electric pulses or in any other suitable fashion (e.g., with sawtooth waveform, sinusoidal waveform, etc.). Other various suitable components, features, configurations, and operabilities that may be associated with stimulation chamber (600) will be apparent to those of ordinary skill in the art in view of the teachings herein. It should also be understood that functionality of stimulation chamber (600) may be integrated into tissue measurement chamber (400) and/or into other components of system (10), if desired. In other words, it should be understood that tissue cells may be ultrasonically stimulated. Various suitable ways in which such functionality may be integrated into tissue measurement chamber (400) and/or into other components of system (10) will also be apparent to those of ordinary skill in the art in view of the teachings herein.

G. Exemplary Fluid Removal Chamber

Figure 12:
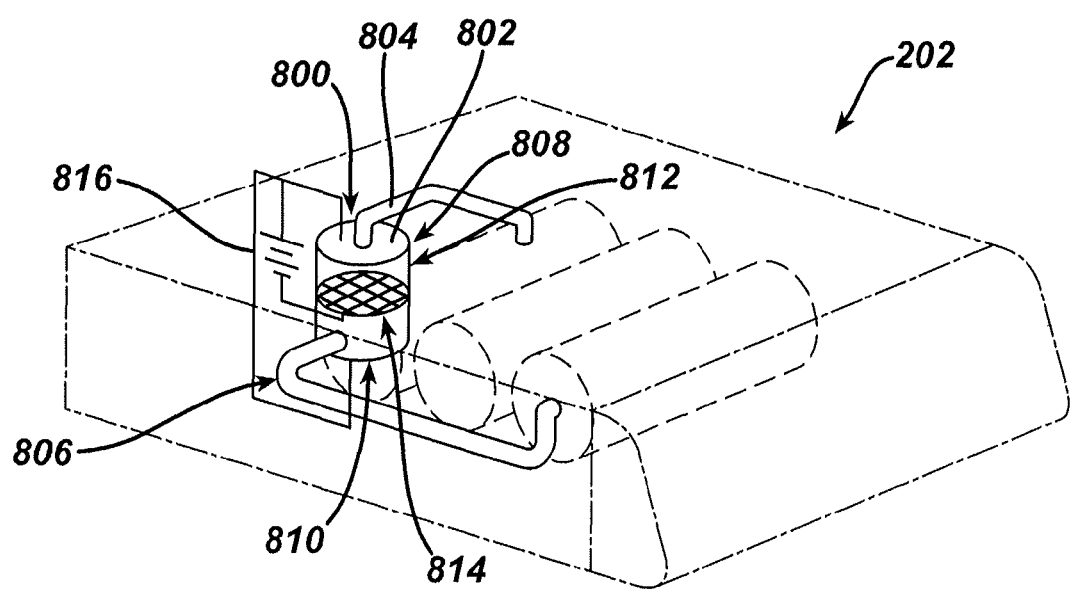
FIG. 12 depicts a perspective view of an exemplary fluid removal chamber of the console of FIG. 5.

After being stimulated in stimulation chamber (600), tissue is communicated to fluid removal chamber (800) in the present example. As shown in FIG. 12, fluid removal chamber (800) comprises a housing (802) that is in fluid communication with an input fluid conduit (804) and an output fluid conduit (806). Housing (802) includes a top portion (808), a bottom portion (810), and a side portion (812) that extends between top portion (808) and bottom portion (810). Top portion (808) and bottom portion (810) each include an electrically conductive material (e.g., a metal, etc.). Side portion (812) is formed of a non-conductive material (e.g., a plastic, etc.). An electrically conductive filter screen (814) is positioned within housing (802), between top portion (808) and bottom portion (810). A DC bias current (816) is applied to top portion (808), bottom portion (810), and filter screen (814), with filter screen (814) having a positive polarity and top and bottom portions (808, 810) having negative polarity. In some versions, due to the polar nature of cellular material, such cellular material within housing (802) may tend to agglomerate around filter screen (814), allowing liquid to be removed through output fluid conduit (806).

Fluid removed through output fluid conduit (806) is communicated to fluid reservoir (1000) in the present example. In some versions, such fluid communicated to fluid reservoir (1000) is used in tissue stirring chamber (300), as described above, in subsequent tissue processing cycles. In addition or in the alternative, such fluid in fluid reservoir (1000) may be driven by fluid pump (1100) to flush harvested tissue from tissue harvesting device (100), as described above, in subsequent tissue processing cycles. In some other versions, fluid removed through output fluid conduit (806) is simply disposed of. Of course, fluid removed through output fluid conduit (806) may be dealt with in any other suitable fashion. In the present example, fluid reservoir (1000) comprises a chamber that is integral within console (200). In some other versions, fluid reservoir (1000) comprises a canister that is removably coupled with console (200) via mating self-sealing ports, via a conduit extending from console (200), or by some other means of coupling. In still other versions, fluid reservoir (1000) is either incorporated into one or more other components of console (200) or is simply omitted altogether.

After fluid is removed by fluid removal chamber (800), the tissue may be communicated to various other locations. For instance, the tissue may be communicated to port (221), through which the tissue may be further communicated to tissue harvesting device (100) and/or to tissue therapy device (101) for administration of the tissue to a patient (e.g., as part of a medical fluid). In some such versions, console (200) also includes a medical fluid chamber (not shown) positioned between fluid removal chamber (800) and port (221). Such a medical fluid chamber may include one or more medical fluid components that may be combined with processed tissue and communicated with the processed tissue to tissue harvesting device (100) and/or to tissue therapy device (101) for administration of the medical fluid mixture to a patient. In addition or in the alternative, a medical fluid chamber may be positioned between console (200) and tissue harvesting device (100) or tissue therapy device (101), such that the processed tissue from console (200) is mixed with the medical fluid on its way to tissue harvesting device (100) or tissue therapy device (101). As yet another variation, a medical fluid chamber may be provided within tissue harvesting device (100) and/or to tissue therapy device (101), such that the processed tissue from console (200) is mixed with the medical fluid once it reaches tissue harvesting device (100) or tissue therapy device (101).

As another merely illustrative example, tissue may be communicated from fluid removal chamber (800) to a tissue container (900). Such a tissue container (900) may comprise a chamber that is integral within console (200). In some other versions, tissue container (900) comprises a canister that is removably coupled with console via mating self-sealing ports, via a conduit extending from console (200), or by some other means of coupling. At least some tissue may be communicated from fluid removal chamber (800) to waste chamber (700), if desired. Still other suitable ways in which tissue from fluid removal chamber (800) may be handled, including but not limited to other components or devices to which such tissue may be communicated, will be apparent to those of ordinary skill in the art in view of the teachings herein.

In some versions, filter screen (814) is removable from housing (802). In particular, filter screen (814) may be removable so that once tissue is fully agglomerated to filter screen (814), filter screen (814) and agglomerated tissue may be removed for further processing. In addition or in the alternative, fluid removal chamber (800) may include a scraper device (not shown) that is operable to at least substantially remove tissue from filter screen (814). For instance, such a scraper device may comprise a rotating scraper that is operable to scrape cells/tissue from filter screen (814) and convey the scraped cells/tissue into a central core at the axis of the scraper. The scraped cells/tissue may then be transmitted to waste chamber (700), tissue container (900), tissue harvesting device (100) and/or tissue therapy device (101) using a plunger, using a relatively small amount of saline or other fluid to flush the cells/tissue, using any other means of conveyance referred to herein, or in any other suitable fashion.

It should also be understood that the screening and removal of fluid may be provided within tissue harvesting device (100) and/or tissue therapy device (101), in addition to or in lieu of being provided within console (200). For instance, fluid removal chamber (800) (or some variation thereof) may be incorporated into tissue harvesting device (100) and/or tissue therapy device (101); and may be used after processed tissue is communicated from console (200) to tissue harvesting device (100) and/or tissue therapy device (101). Of course, fluid removal chamber (800) as described above is only one example of how fluid may be removed from tissue. It should be understood that one or more other components of console (200) may remove fluid from tissue, including but not limited to tissue measuring chamber (400, 401, 450). To the extent that a fluid removal chamber (800) is included as a part of console (200), other suitable components, features, configurations, and operabilities of fluid removal chamber (800) will be apparent to those of ordinary skill in the art in view of the teachings herein.

H. Exemplary Control Logic

As noted above, control circuitry (250) of the present example is configured to control various components (300, 400, 500, 600, 800, 1110) in accordance with user inputs via control panel (240) and/or in accordance with predefined control algorithms or routines. It should also be understood that console (200) may include various sensors (not shown) in communication with control circuitry (250), and that various conditions detected by such sensors may trigger various types of responses from control logic in control circuitry (250). By way of example only, a sensor may be configured to detect the coupling of tissue harvesting device (100) with console (200), and may be further configured to communicate data indicative of the same to control circuitry (250). Various suitable ways in which such a sensor may be configured and positioned will be apparent to those of ordinary skill in the art in view of the teachings herein. In addition, a sensor may be configured to detect the presence of tissue within measuring chamber (400), and may be further configured to communicate data indicative of the same to control circuitry (250). By way of example only, such a sensor may be provided by drive transducer (416). Alternatively, some other sensor may be used to detect the presence of tissue within measuring chamber (400) while drive transducer (416) is then used to measure the size of tissue particles within measuring chamber (400).

Various other suitable ways in which such a sensor may be configured and positioned will be apparent to those of ordinary skill in the art in view of the teachings herein.

In addition, a sensor may be configured to detect the presence of tissue within mincing chamber (500), and may be further configured to communicate data indicative of the same to control circuitry (250). Various suitable ways in which such a sensor may be configured and positioned will be apparent to those of ordinary skill in the art in view of the teachings herein. A sensor may also be configured to detect the presence of tissue within fluid removal chamber (800), and may be further configured to communicate data indicative of the same to control circuitry (250). Various suitable ways in which such a sensor may be configured and positioned will also be apparent to those of ordinary skill in the art in view of the teachings herein. In addition, a sensor may be configured to detect the level of fluid within fluid reservoir (1000) (e.g., when fluid reservoir (1000) is empty), and may be further configured to communicate data indicative of the same to control circuitry (250). Various suitable ways in which such a sensor may be configured and positioned will also be apparent to those of ordinary skill in the art in view of the teachings herein. In addition, a sensor may be configured to detect an amount of waste in waste chamber (700) (e.g., when waste chamber (700) is full), and may be further configured to communicate data indicative of the same to control circuitry (250). Various suitable ways in which such a sensor may be configured and positioned will also be apparent to those of ordinary skill in the art in view of the teachings herein. Of course, various other types of sensors may be provided in various other locations within tissue processing system (10), and such sensors may detect a variety of conditions. Various ways in which such additional/alternative sensors may be incorporated into tissue processing system (10) will be apparent to those of ordinary skill in the art in view of the teachings herein.

It should be understood that logic in control circuitry (250) may react in a variety of ways in response to conditions detected by sensors within tissue processing system (10). The below table illustrates several merely illustrative examples of operational responses that logic in control circuitry (250) may provide based on one or more conditions detected by sensors in tissue processing system (10).

| Condition Sensed | Action(s) Taken |
| --- | --- |
| Tissue harvesting device (100) coupled with console (200) | Liquid (e.g., saline) flushed through tissue harvesting device (100) into tissue stirring chamber (300) and/or measurement chamber (400). |
| Tissue present in measuring chamber (400) | Activate measuring chamber (400) to de-aerate tissue/fluid mixture. Activate measuring chamber (400) to measure tissue particle size. Transfer oversized tissue particles to mincing chamber (500). |
| Tissue present in mincing chamber (500) | Activate mincing chamber (500) to mince tissue. Transfer minced tissue back to measuring chamber (400). Transfer appropriately sized tissue to stimulation chamber (600) and/or fluid removal chamber (800). |
| Tissue present in fluid removal chamber (800) | Activate DC bias in fluid removal chamber (800). Measure tissue particle mass. Transfer tissue to tissue harvesting device (100) and/or tissue therapy device (101). |
| Fluid reservoir (1000) at or near empty | Activate alert on display (242). |
| Waste chamber (700) at or near full | Activate alert on display (242). |

Still other suitable operational responses (or other types of responses) that logic in control circuitry (250) may provide based on one or more conditions detected by sensors in tissue processing system (10) will be apparent to those of ordinary skill in the art in view of the teachings herein. Similarly, various other types of conditions that may be sensed by sensors to trigger responses by control circuitry (250) will be apparent to those of ordinary skill in the art in view of the teachings herein.

V. Miscellaneous

As shown in FIGS. 2 and 5, waste chamber (700), tissue container (900) (not shown in FIG. 5), and fluid reservoir (1000) each comprise a canister in the present example; and are all located external to housing (202) of console (200). These components (700, 900, 1000) are instead externally coupled with a base (204) at the side of housing (202). In particular, these components (700, 900, 1000) and base (204) all comprise respective ports that are configured to provide fluid communication between these components (700, 900, 1000) and console (200) when these components (700, 900, 1000) are coupled with base (204); and that are further configured to provide a substantially fluid tight seal when these components (700, 900, 1000) are de-coupled from base (204). Such ports may thus be configured similar to ports (120, 121, 220, 221) described above or be otherwise configured.

Positioning these components (700, 900, 1000) external to housing (202) may facilitate removal of these components (700, 900, 1000) for emptying of these components (700, 900, 1000) and/or for replacement of these components (700, 900, 1000). It should be understood that each of these components (700, 900, 1000) may include a cap, a septum, and/or some other type of seal that can be used to prevent fluid leakage from components (700, 900, 1000) when any of these components (700, 900, 1000) are removed from base (204). In addition or in the alternative, each port on base (204) associated with components (700, 900, 1000) may include a cap, a septum, and/or some other type of seal that can be used to prevent fluid leakage from base (204) when any of these components (700, 900, 1000) are removed from base (204).

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from suitable metals, ceramics, plastics, or combinations thereof. Furthermore, although not required, the construction of devices described herein may be configured to be compatible with or optimize their use with various imaging technologies. For instance, a device configured for use with MRI may be constructed from all non-ferromagnetic materials. Also for instance, when using optional imaging technologies with devices described herein, certain configurations may include modifications to materials of construction such that portions or the device may readily appear in a resultant image. Various suitable ways in which these and other modifications to the construction of devices described herein may be carried out will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by those of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A device for measuring tissue particle size, wherein the device comprises:
    (a) a housing;
    (b) a reservoir defined by the housing;
    (c) an ultrasonic transducer in communication with the reservoir;
    (d) control circuitry in communication with the ultrasonic transducer, wherein the control circuitry is operable to drive the ultrasonic transducer to emit ultrasonic energy toward tissue particles in the reservoir, wherein the control circuitry is further operable to process received ultrasonic energy data to determine the size of tissue particles in the reservoir; and
    (e) a fluid removal chamber, wherein the fluid removal chamber is operable to separate the tissue particles from a fluid, wherein the control circuitry is further operable to provide communication of tissue particles from the reservoir to the fluid removal chamber based at least in part on the determined size of the tissue particles in the reservoir.

2. The device of claim 1, further comprising a receiving transducer in communication with the reservoir, wherein the receiving transducer is in further communication with the control circuitry to provide data signals indicative of the received ultrasonic energy to the control circuitry.

3. The device of claim 2, wherein the reservoir is defined in part by a first end of the housing and a second end of the housing, wherein the ultrasonic transducer is positioned at the first end of the housing, wherein the receiving transducer is positioned at the second end of the housing.

4. The device of claim 1, further comprising a console, wherein the console is configured to couple with a tissue harvesting device and transmit tissue harvested by the tissue harvesting device to the reservoir.

5. The device of claim 1, further comprising a mincing chamber in communication with the reservoir, wherein the mincing chamber is operable to mince tissue.

6. The device of claim 5, wherein the mincing chamber comprises an ultrasonic member operable to mince tissue through ultrasonic energy.

7. The device of claim 5, wherein the control circuitry is further operable to provide communication of tissue particles from the reservoir to the mincing chamber based at least in part on the determined size of the tissue particles in the reservoir.

8. The device of claim 5, wherein the control circuitry is further operable to provide communication of tissue particles from the mincing chamber back to the reservoir after the mincing chamber has minced the tissue particles.

9. The device of claim 1, further comprising a waste container, wherein the control circuitry is further operable to provide communication of tissue particles from the reservoir to the waste container based at least in part on the determined size of the tissue particles in the reservoir.

10. The device of claim 1, further comprising a tissue stimulation chamber, wherein the tissue stimulation chamber is operable to stimulate tissue particles using one or both of electrical energy or ultrasonic energy.

11. The device of claim 10, wherein the tissue stimulation chamber is positioned in a fluid path between the reservoir and the fluid removal chamber.

12. The device of claim 1, further comprising an absorbent medium configured to absorb fluid, wherein the absorbent medium is in selective communication with the reservoir.

13. The device of claim 12, wherein the reservoir is defined in part by a first end of the housing, a second end of the housing, and a sidewall extending between the first and second ends, wherein at least part of the absorbent medium is located in the sidewall.

14. The device of claim 12, wherein the reservoir is defined in part by a first end of the housing, a second end of the housing, and a sidewall extending between the first and second ends, wherein at least part of the absorbent medium is located in the first end or the second end.

15. The device of claim 12, further comprising a movable plunger in the reservoir, wherein the plunger is movable to selectively expose at least a portion of the absorbent medium to fluid in the reservoir.

16. A device for measuring and reducing tissue particle size, wherein the device comprises:
 (a) a tissue measurement chamber, wherein the tissue measurement chamber comprises:
  (i) a reservoir configured to hold tissue,
  (ii) an ultrasonic transducer in communication with the reservoir, wherein the ultrasonic transducer is operable to emit ultrasonic energy in the reservoir;
 (b) a tissue mincing chamber, wherein the tissue mincing chamber is in selective communication with the reservoir, wherein the tissue mincing chamber is operable to mince tissue; and
 (c) control circuitry in communication with the tissue measurement chamber, wherein the control circuitry is further in communication with the tissue mincing chamber, wherein the control circuitry is configured to determine the size of tissue particles in the reservoir based at least in part on detected ultrasonic energy emitted by the ultrasonic transducer, wherein the control circuitry is further operable to provide communication of tissue from the reservoir to the tissue mincing chamber based at least in part on determined tissue particle size.

17. The device of claim 16, wherein the ultrasonic transducer is operable to emit pulses of ultrasonic energy configured to move tissue particles from the reservoir to the tissue mincing chamber.

18. A method of processing tissue in a tissue processing device, the method comprising:
 (a) emitting ultrasonic energy toward tissue, wherein the tissue is located in a measurement chamber;
 (b) receiving at least a portion of the ultrasonic energy;
 (c) processing the received ultrasonic energy to determine the size of particles of the tissue; and
 (d) transmitting the particles of the tissue to a second chamber based at least in part of the determined size of the particles of the tissue.

19. The method of claim 18, further comprising mincing the particles of the tissue based at least in part of the determined size of the particles of the tissue.

* * * * *